United States Patent
Campbell et al.

(10) Patent No.: US 9,390,238 B2
(45) Date of Patent: Jul. 12, 2016

(54) WINDOWING COMBINED WITH ION-ION REACTIONS FOR CHEMICAL NOISE ELIMINATION

(71) Applicant: DH TECHNOLOGIES DEVELOPMENT PTE. LTD., Singapore (SG)

(72) Inventors: John Lawrence Campbell, Milton (CA); Yves Le Blanc, Newmarket (CA); Alexandre V. Loboda, Thornhill (CA); Igor Chernushevich, Toronto (CA)

(73) Assignee: DH Technologies Development Pte. Ltd., Singapore (SG)

( * ) Notice: Subject to any disclaimer, the term of this patent is extended or adjusted under 35 U.S.C. 154(b) by 156 days.

(21) Appl. No.: 14/365,983

(22) PCT Filed: Nov. 28, 2012

(86) PCT No.: PCT/IB2012/002530
§ 371 (c)(1),
(2) Date: Jun. 16, 2014

(87) PCT Pub. No.: WO2013/098603
PCT Pub. Date: Jul. 4, 2013

(65) Prior Publication Data
US 2014/0357502 A1   Dec. 4, 2014

Related U.S. Application Data

(60) Provisional application No. 61/582,228, filed on Dec. 30, 2011.

(51) Int. Cl.
*H01J 49/00* (2006.01)
*G06F 19/00* (2011.01)

(52) U.S. Cl.
CPC .............. *G06F 19/703* (2013.01); *H01J 49/004* (2013.01); *H01J 49/0031* (2013.01)

(58) Field of Classification Search
CPC .... G06F 19/703; H01J 49/004; H01J 49/0031
USPC .................................................. 250/281, 282
See application file for complete search history.

(56) References Cited

U.S. PATENT DOCUMENTS

| | | | | |
|---|---|---|---|---|
| 2009/0256073 A1* | 10/2009 | Guo | .................. | G01N 33/6848 250/288 |
| 2009/0299653 A1* | 12/2009 | Pfaff | ...................... | G06F 19/12 702/28 |
| 2011/0057098 A1* | 3/2011 | Le Blanc | ............ | H01J 49/4295 250/283 |

(Continued)

FOREIGN PATENT DOCUMENTS

EP      0519047 B1     10/1996
EP      1672673 A2      6/2006

(Continued)

OTHER PUBLICATIONS

International Search Report for PCT/IB2012/002530, mailed Apr. 30, 2013.

*Primary Examiner* — Michael Maskell
(74) *Attorney, Agent, or Firm* — John R. Kasha; Kelly L. Kasha; Kasha Law LLC

(57) ABSTRACT

In a first location of a mass spectrometer, a plurality of ionized molecules of an ion source are selected that have mass-to-charge ratios within a mass-to-charge ratio window width. The plurality of selected ionized molecules are transmitted from a first to a second location. Reagent ions are transmitted to the second location to reduce a charge state of one or more of the plurality of selected ionized molecules. A mass analyzer is used to analyze the plurality of reduced ionized molecules and produce a mass spectrum. A compound is identified from a peak of the spectrum that has a mass-to-charge ratio less than or equal to the highest mass-to-charge ratio in the window width if the noise is multiply charged and greater than the highest mass-to-charge ratio in the window width if the noise is singly charged.

8 Claims, 17 Drawing Sheets

(56) References Cited

U.S. PATENT DOCUMENTS

2011/0114835 A1* 5/2011 Chen .................. H01J 49/0072
250/282

FOREIGN PATENT DOCUMENTS

| JP | 2004-132946 A | 4/2004 |
| WO | 2008-142170 A1 | 11/2008 |

* cited by examiner

US 9,390,238 B2

WINDOWING COMBINED WITH ION-ION REACTIONS FOR CHEMICAL NOISE ELIMINATION

RELATED APPLICATIONS

This application claims the benefit and priority from U.S. Provisional Application Ser. No. 61/582,228, filed on Dec. 30, 2011, the entire contents of which is incorporated by reference herein.

FIELD

The teachings described herein relate to methods and devices for noise elimination in mass spectrometers using a windowing method.

BACKGROUND

The rapidly increasing sensitivity of mass spectrometers does not automatically solve the problem of finding low-abundance components in the forest of chemical noise. Various separation techniques, such as liquid chromatography (LC), mobility, or field asymmetric waveform ion mobility spectrometry (FAIMS), used in front of a mass analyzer can reduce chemical noise. However, in complex mixtures, components present at concentrations below 10-8 M can still be difficult to detect.

For example when mixtures of peptides or intact proteins are subjected to electrospray ionization (ESI), the resulting mass spectra are heavily convoluted These compounds form many multiply charged analogues (e.g., +2 to +20) that can be compacted into only a small portion of the m/z scale, quite often the same m/z space as chemical noise ions. This makes analysis and elucidation of individual species quite difficult.

BRIEF DESCRIPTION OF THE DRAWINGS

The skilled person in the art will understand that the drawings, described below, are for illustration purposes only. The drawings are not intended to limit the scope of the applicant's teachings in any way.

Figure 1:
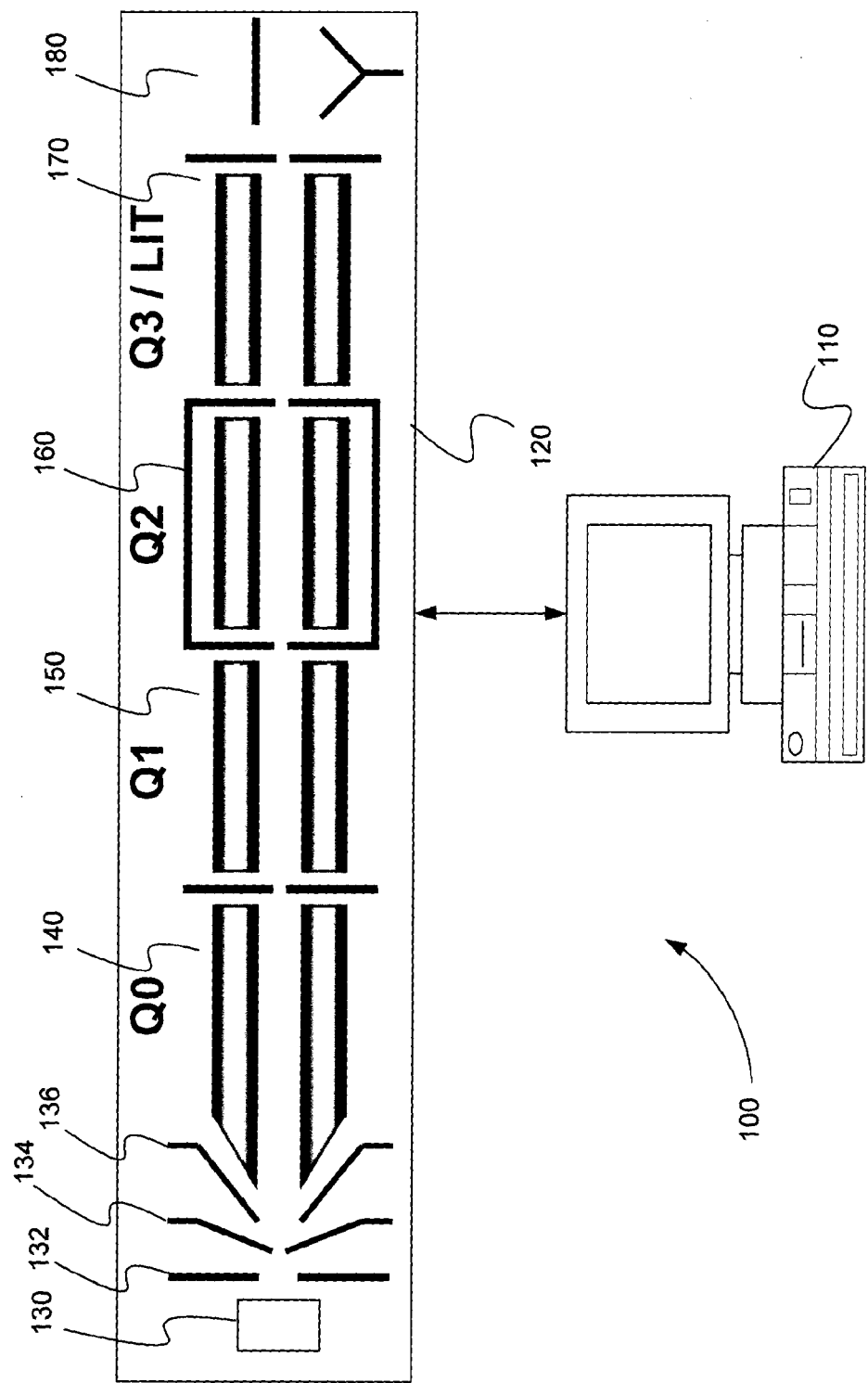
FIG. 1 is a schematic diagram that illustrates a system for targeted ion parking that includes a hybrid quadrupole linear ion trap system (QqQLIT), in accordance with various embodiments.

Before one or more embodiments of the invention are described in detail, one skilled in the art will appreciate that the invention is not limited in its application to the details of construction, the arrangements of components, and the arrangement of steps set forth in the following detailed description or illustrated in the drawings. The invention is capable of other embodiments and of being practiced or being carried out in various ways. Also, it is to be understood that the phraseology and terminology used herein is for the purpose of description and should not be regarded as limiting.

DESCRIPTION OF VARIOUS EMBODIMENTS

The section headings used herein are for organizational purposes only and are not to be construed as limiting the subject matter described in any way.

Methods of Data Processing
Ion Parking

Electrospray ionization (ESI) and other ionization methods can produce multiply-charged analyte ions from large molecules including peptides and proteins. This permits certain analysis of high mass molecules by a mass spectrometer having a lower mass-to-charge range. It is also known that introducing counter ions of opposite charge, including singly-charged counter ions, which can react by ion to ion charge transfer reactions, including proton transfer reactions, will migrate the analyte ions to lesser multiple charged states that represent higher mass-to-charge ratios. Ion parking is a method of controlling the ion to ion transfer reactions for practical use in mass spectrometry. Conventionally, ion parking involves inhibiting the rate of ion to ion transfer reactions in a selective fashion such that particular ions are preferentially retained or accumulated, while ions that are not selected can undergo unperturbed reactions up to neutralization.

U.S. Pat. No. 6,627,875 to Afeyan et. al. (the "Afeyan patent") discloses a method of ion parking using a three-dimensional ion trap. In this method, a tailored waveform is applied to the endcap electrodes of the three-dimensional ion trap to segregate a subset of ionized molecules from sample molecules. Reagent ions are reacted with the subset of ionized molecules to reduce the charge state of the subset of ionized molecules. Reduced ionized molecules having the highest mass-to-charge ratio are detected. These steps are then repeated in the same physical space, chamber, or location for another tailored waveform until a mass spectrum is defined. One disadvantage of performing ion parking in the same physical space, chamber, or location is decreased selectivity. All molecules within the subset of ionized molecules are charge reduced together. As a result, noise or species in between masses of interest are parked along with the masses of interest reducing selectivity.

In various embodiments, systems and methods perform ion parking on a "selective subset" of the plurality of ions generated from an ion source. Therefore, ions predominantly corresponding to the compound of interest are selected prior to ion parking. The ions corresponding to the compound of interest can be selected based on a number of ion characteristics. One ion characteristic is mass. In mass based selection a mass analyzer is used to select the ions of interest prior to ion parking. A mass analyzer can include, but is not limited to, a quadrupole or a trap.

Another ion characteristic that can be used for the selection is mobility. In mobility based selection a mobility cell is used to select the ions of interest prior to ion parking. Multiply charged ions have been shown to have mobilities that can be significantly different between species. Multiply charged ions can include, but are not limited to, proteins or peptides. A mobility cell can include, but is not limited to, a low field mobility cell, a differential mobility analyzer (DMA), a differential mobility spectrometry (DMS) cell, or a field asymmetric waveform ion mobility spectrometry (FAIMS) cell.

FIG. 1 is a schematic diagram that illustrates a system 100 for targeted ion parking that includes a hybrid quadrupole linear ion trap system (QqQLIT), in accordance with various embodiments. System 100 includes processor 110 and mass spectrometer 120. Processor 110 is in two-way communication with mass spectrometer 120. Processor 110 can be, but is not limited to, a computer, microprocessor, or any device capable of sending and receiving data and control signals to and from mass spectrometer 120 and processing information.

Processor 110 receives a group of mass-to-charge ratios to be targeted or isolated. Processor 110 also receives a charge state reduction amount. Processor 110 receives these values from a user, for example. The charge state reduction amount is the number of charges (z) by which the targeted ionized molecules of the sample will be reduced, consequently increasing the observed m/z (mass to charge ratio) associated with the ionized molecule of the sample.

Under the control of processor 110, mass spectrometer 120 performs targeted ion parking based on ion mass. The ionized molecules of the sample are created by ionization device 130 of mass spectrometer 120. The ionized molecules pass through curtain plate 132, orifice 134, and skimmer 136 to reach quadrupole 140. Quadrupole 140 is used to focus the ionized molecules. Quadrupole 150 selects and transmits a subset of ionized molecules of the sample corresponding to each of the mass-to-charge ratios received by processor 110 from quadrupole 150 to quadrupole 160.

Quadrupole 150 can be, for example, a quadrupole ion guide or mass filter. Quadrupole 160 is, for example, a collision cell. Processor 110, for example, can be used to vary the radio frequency direct current (RFDC) voltage applied to quadrupole 150 to transmit sequentially each subset of ionized molecules of the sample corresponding to each of the mass-to-charge ratios to be targeted.

Each subset of ionized molecules of the sample transmitted by quadrupole 150 is accumulated in quadrupole 160. Reagent ions are transmitted into quadrupole 160 to charge reduce the accumulated ionized molecules. The charge reduction reaction in quadrupole 160 is stopped at the charge state reduction amount, producing a plurality of parked targeted ions in quadrupole 160. As a result, in system 100 the ionized molecules are mass selected and parked in separate locations, quadrupole 150 and quadrupole 160, respectively.

Charge reduction is stopped for the compound of interest by inhibition of the reaction. This is done, for example, by resonant excitation at an m/z associated with the compound of interest. Here z represents the reduced charge for the compound of interest. Because z has a lower value after the reduction and m (mass) is constant for a given compound, parking occurs at a higher m/z value. Other ions continued to react until they are moved to the next stage of analysis. In other words, the reaction proceeds for finite amount of time. Typically, the allowed reaction time is set to a few tens of milliseconds. After that time period, all ions are transferred to a mass analysis section, for example, and reagent ions move in a direction opposite to the direction of ions of the compound of interest.

Quadrupole 160 is the preferred location for charge reduction and ion parking, because performing these operations at higher pressure can improve efficiency and speed. Typically, quadrupole 140 and 160 have much higher pressures than quadrupole 150 and chamber 170, for example. The pressures in quadrupole 140 and 160 are on the order of 1-10 milli-Torr, for example. The pressures in quadrupole 150 and chamber 170 are on the order of 10-100 micro-Torr, for example.

The reagent ions follow a similar path as the ionized molecules of the sample to quadrupole 160. The reagent ions are, for example, transmitted by quadrupole 150 to quadrupole 160. The targeted ions and reagent ions are introduced sequentially, for example.

After the targeted ions are charged reduced and parked, they are transferred from quadrupole 160 to quadrupole 170 for additional ion processing. Additional ion processing can include, but is not limited to, mass analysis or fragmentation.

In various alternative embodiments, quadrupole 150 selects and transmits a subset of the sample of ionized molecules corresponding to each of the mass-to-charge ratios received by processor 110 from quadrupole 150 through quadrupole 160 to chamber 170. Each subset of ionized molecules of the sample transmitted by quadrupole 150 is accumulated in chamber 170. Reagent ions are transmitted into quadrupole 170 to charge reduce the accumulated ionized molecules. The charge reduction in chamber 170 is stopped at the charge state reduction amount, producing a plurality of parked targeted ions chamber 170. As a result, in this embodiment the ionized molecules are mass selected by quadrupole 150 and parked in ion chamber 170.

Chamber 170 can be used to determine a mass spectrum from the reduced ionized molecules accumulated in quadrupole 160 or chamber 170. Chamber 170 can be, but is not limited to, a quadrupole, an ion trap, or a linear ion trap mass spectrometer, for example. Detector 180 is used to detect the parked target ions, for example.

Figure 2:
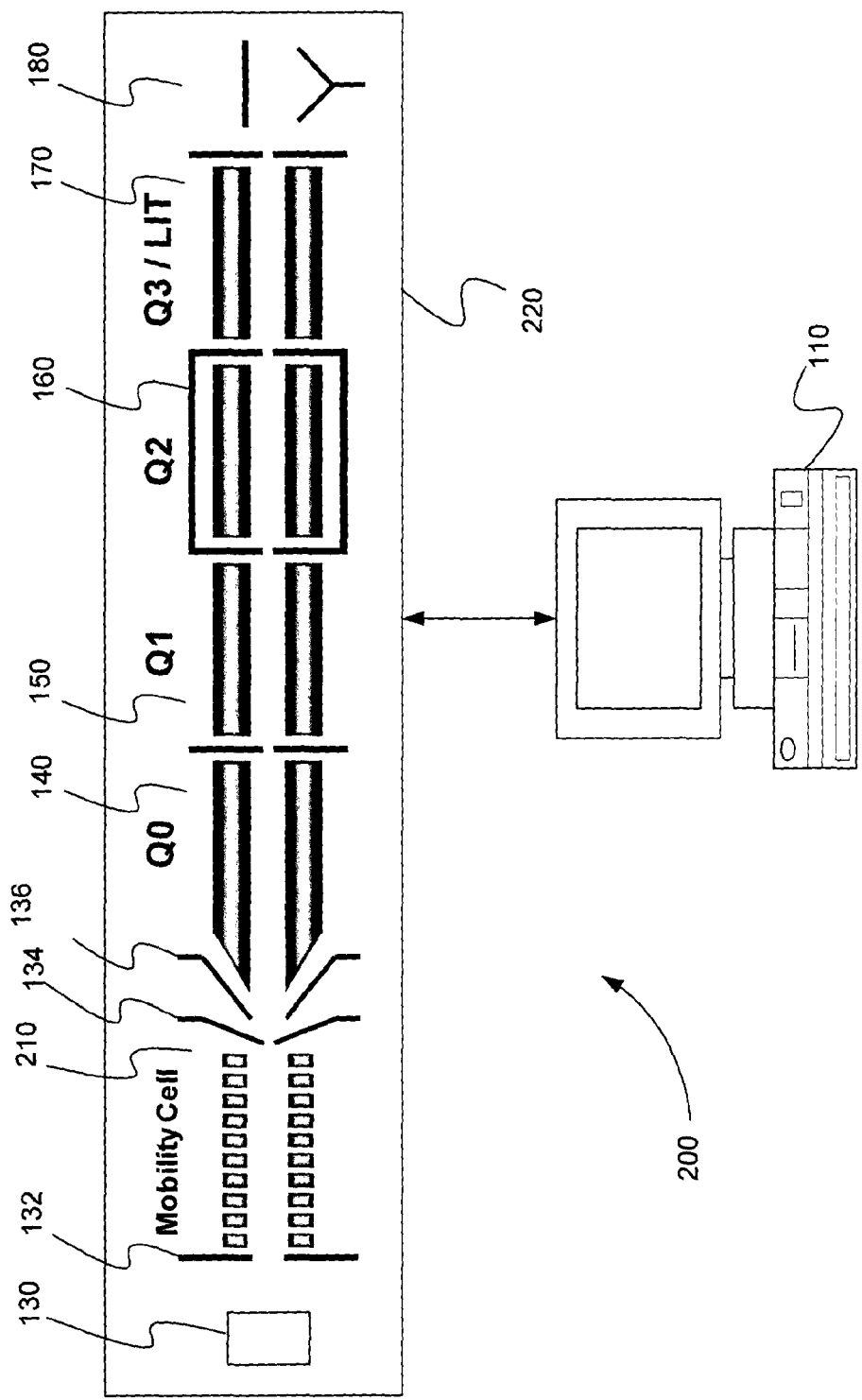
FIG. 2 is a schematic diagram that illustrates a system for targeted ion parking that includes a mobility cell and a hybrid quadrupole linear ion trap (QqQLIT) system, in accordance with various embodiments.

FIG. 2 is a schematic diagram that illustrates a system 200 for targeted ion parking that includes a mobility cell and a hybrid quadrupole linear ion trap system (QqQLIT), in accordance with various embodiments.

System 200 includes processor 110 and mass spectrometer 220. Processor 110 receives a group of ion mobilities to be targeted or isolated. Processor 110 also receives a charge state reduction amount.

Under the control of processor 110, mass spectrometer 220 performs targeted ion parking based on ion mobility. The ionized molecules of the sample are created by ionization device 130 of mass spectrometer 220. The ionized molecules pass through curtain plate 132 and into mobility cell 210. Mobility cell 210 is used to select a subset of ionized molecules of the sample corresponding to each of the ion mobilities received by processor 110. Mobility cell 210 is located before orifice 134 and is not under vacuum. As a result, the selection of the subset of ionized molecules based on ion mobility is at atmospheric pressure. Placing mobility cell 210 before vacuum chambers can increase its efficiency.

The subset of mobility selected ionized molecules pass through orifice 134 and skimmer 136 to reach quadrupole 140. Quadrupole 140 is used to focus the ionized molecules. Quadrupole 150 transmits the subset of ionized molecules from quadrupole 150 to quadrupole 160. For example, processor 110 operates quadrupole 150 in radio frequency (RF) mode only, so no mass selection is performed by quadrupole 150. Each subset of ionized molecules of the sample transmitted by quadrupole 150 is accumulated in quadrupole 160. Reagent ions are transmitted into quadrupole 160 to charge reduce the accumulated ionized molecules. The charge reduction in quadrupole 160 is stopped at the charge state reduction amount, producing a plurality of parked targeted ions in quadrupole 160. As a result, in system 200 the ionized molecules are mobility selected and parked in separate locations, mobility cell 210 and quadrupole 160, respectively.

After the targeted ions are charged reduced and parked, they are transferred from quadrupole 160 to quadrupole 170 for additional ion processing. Additional ion processing can include, but is not limited to, mass analysis or fragmentation.

In various embodiments and as described above, charge reduction and ion parking can also occur in chamber 170. In these embodiments the ionized molecules are mobility selected in mobility cell 210 and parked in chamber 170.

In various embodiments, system 200 is used to perform targeted ion parking based on both ion mass and ion mobility. Processor 110 receives a group of ion mobilities and a group of mass-to-charge ratios to be targeted or isolated. Processor 110 also receives a charge state reduction amount.

Under the control of processor 110, mass spectrometer 220 performs targeted ion parking based on ion mobility and ion mass. The ionized molecules of the sample are created by ionization device 130 of mass spectrometer 220. The ionized molecules pass through curtain plate 132 and into mobility cell 210. Mobility cell 210 is used to select a subset of ionized molecules of the sample corresponding to each of the ion mobilities received by processor 110.

The subset of mobility selected ionized molecules pass through orifice 134 and skimmer 136 to reach quadrupole 140. Quadrupole 140 is used to focus the ionized molecules. Quadrupole 150 selects and transmits a subset of the mobility selected ionized molecules corresponding to each of the mass-to-charge ratios received by processor 110 from quadrupole 150 to quadrupole 160. Each subset of ionized molecules transmitted by quadrupole 150 is accumulated in quadrupole 160. Reagent ions are transmitted into quadrupole 160 to charge reduce the accumulated ionized molecules. The charge reduction in quadrupole 160 is stopped at the charge state reduction amount, producing a plurality of parked targeted ions in quadrupole 160. As a result, in this embodiment of system 200 the ionized molecules are mobility selected, mass selected, and parked in separate locations, mobility cell 210, quadrupole 150, and quadrupole 160, respectively.

Figure 3:
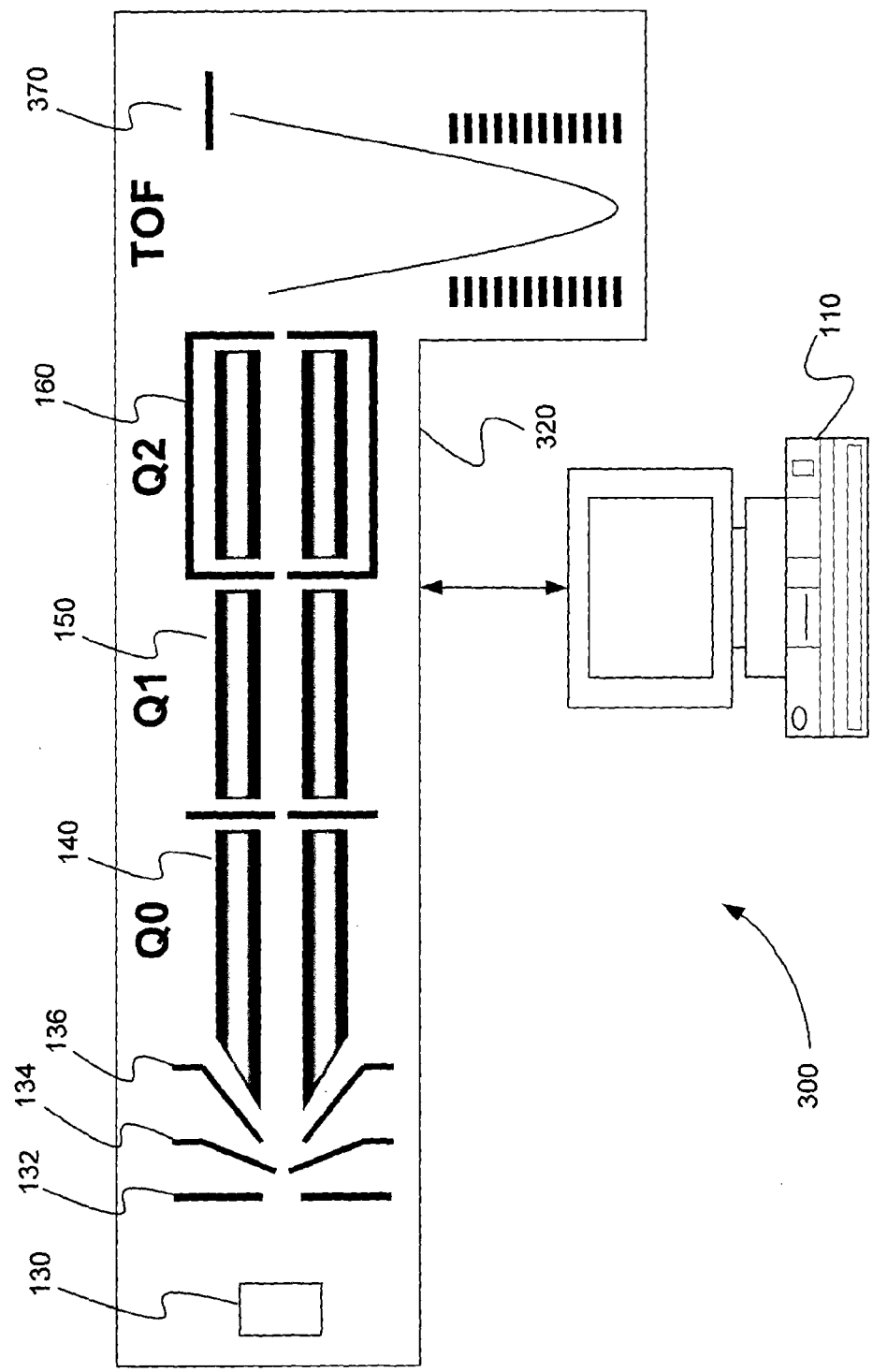
FIG. 3 is a schematic diagram that illustrates a system for targeted ion parking that includes a hybrid quadrupole time-of-flight (QqTOF) system, in accordance with various embodiments.
Figure 4:
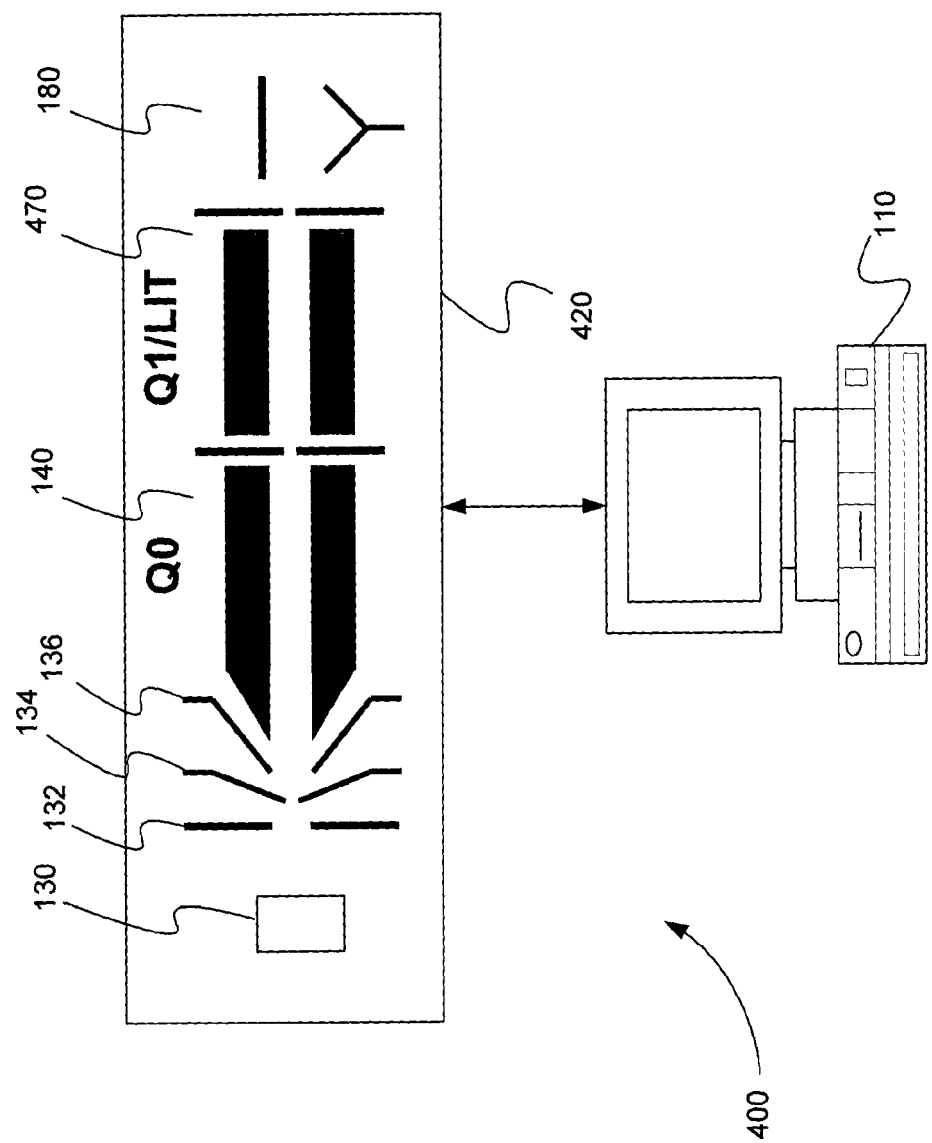
FIG. 4 is a schematic diagram that illustrates a system for targeted ion parking that includes a quadrupole linear ion trap (QLIT) system, in accordance with various embodiments.
Figure 5:
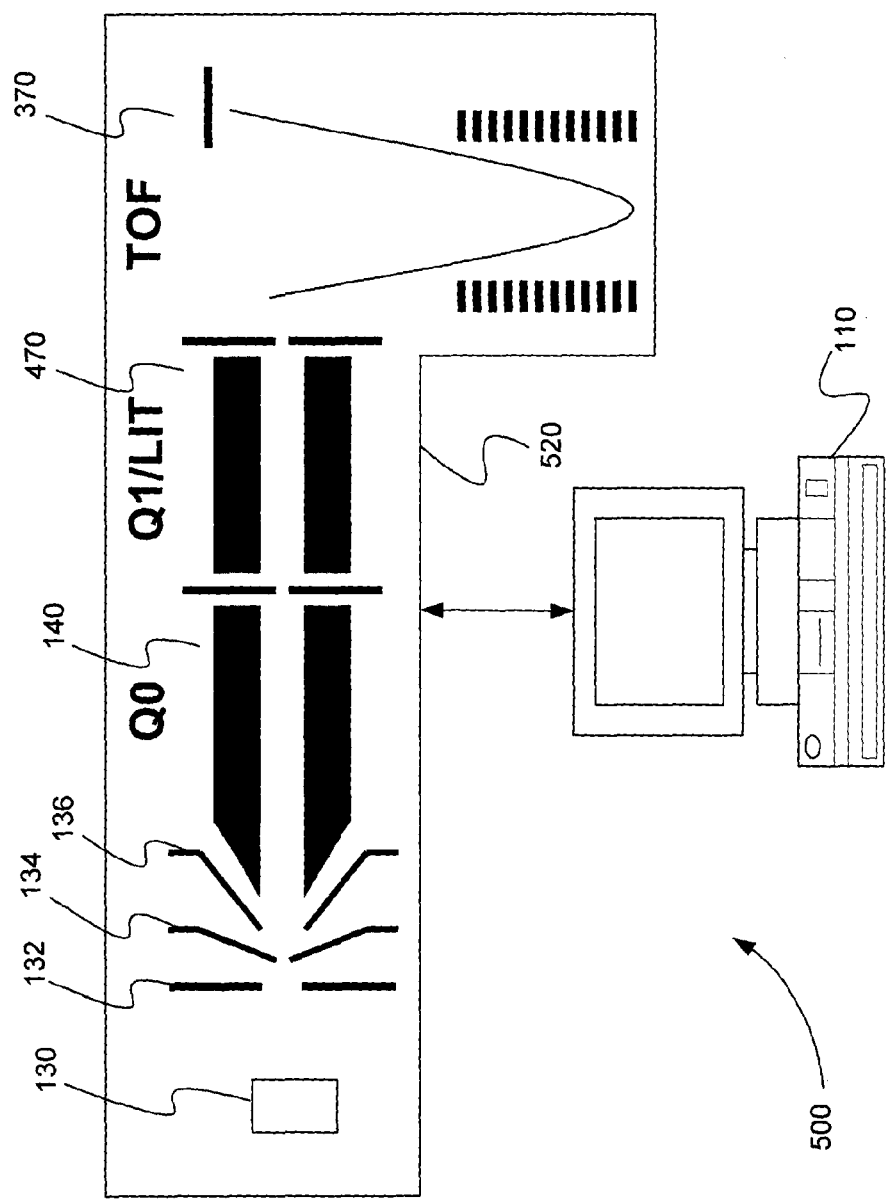
FIG. 5 is a schematic diagram that illustrates a system for targeted ion parking that includes a quadrupole linear ion trap time-of-flight (QLITTOF) system, in accordance with various embodiments.

Numerous mass spectrometer configurations that can provide targeted ion parking based on ion mobility, ion mass, or both ion mobility and ion mass are possible. FIGS. 3-5 depict exemplary mass spectrometer configurations for targeted ion parking based on ion mass. FIGS. 6-12 depict exemplary mass spectrometer configurations for targeted ion parking based on ion mobility or both ion mobility and ion mass.

FIG. 3 is a schematic diagram that illustrates a system 300 for targeted ion parking that includes a hybrid quadrupole time-of-flight (QqTOF) mass spectrometer 320, in accordance with various embodiments. In system 300, quadrupole 150 is used to select and transmit a subset of the ionized molecules of a sample based on ion mass to quadrupole 160, where the subset of the ionized molecules is charge reduced and parked, for example. Time-of-flight (TOF) chamber 370 is used for mass analysis or fragmentation, for example.

FIG. 4 is a schematic diagram that illustrates a system 400 for targeted ion parking that includes a quadrupole linear ion trap (QLIT) mass spectrometer 420, in accordance with various embodiments. In system 400, chamber 470 is used to select and transmit a subset of the ionized molecules of a sample based on ion mass to quadrupole 140, where the subset of the ionized molecules is charge reduced and parked, for example. Linear ion trap (LIT) chamber 470 is used for mass analysis or fragmentation, for example.

In various embodiments of system 400, targeted ion parking can also be performed in chamber 470. Quadrupole 140, however, is the preferred location for ion parking, because the higher pressure of quadrupole 140 can improve efficiency and speed. System 400 is essentially a lower cost version of system 100 of FIG. 1 and can perform similar functions by manipulating ions back-and-forth between quadrupole 140 and chamber 470.

FIG. 5 is a schematic diagram that illustrates a system 500 for targeted ion parking that includes a quadrupole linear ion trap time-of-flight (QLITTOF) mass spectrometer 520, in accordance with various embodiments. In system 500, chamber 470 is used to select and transmit a subset of the ionized molecules of a sample based on ion mass to quadrupole 140, where the subset of the ionized molecules is charge reduced and parked, for example. Time-of-flight (TOF) chamber 370 is used for mass analysis or fragmentation, for example.

Figure 6:
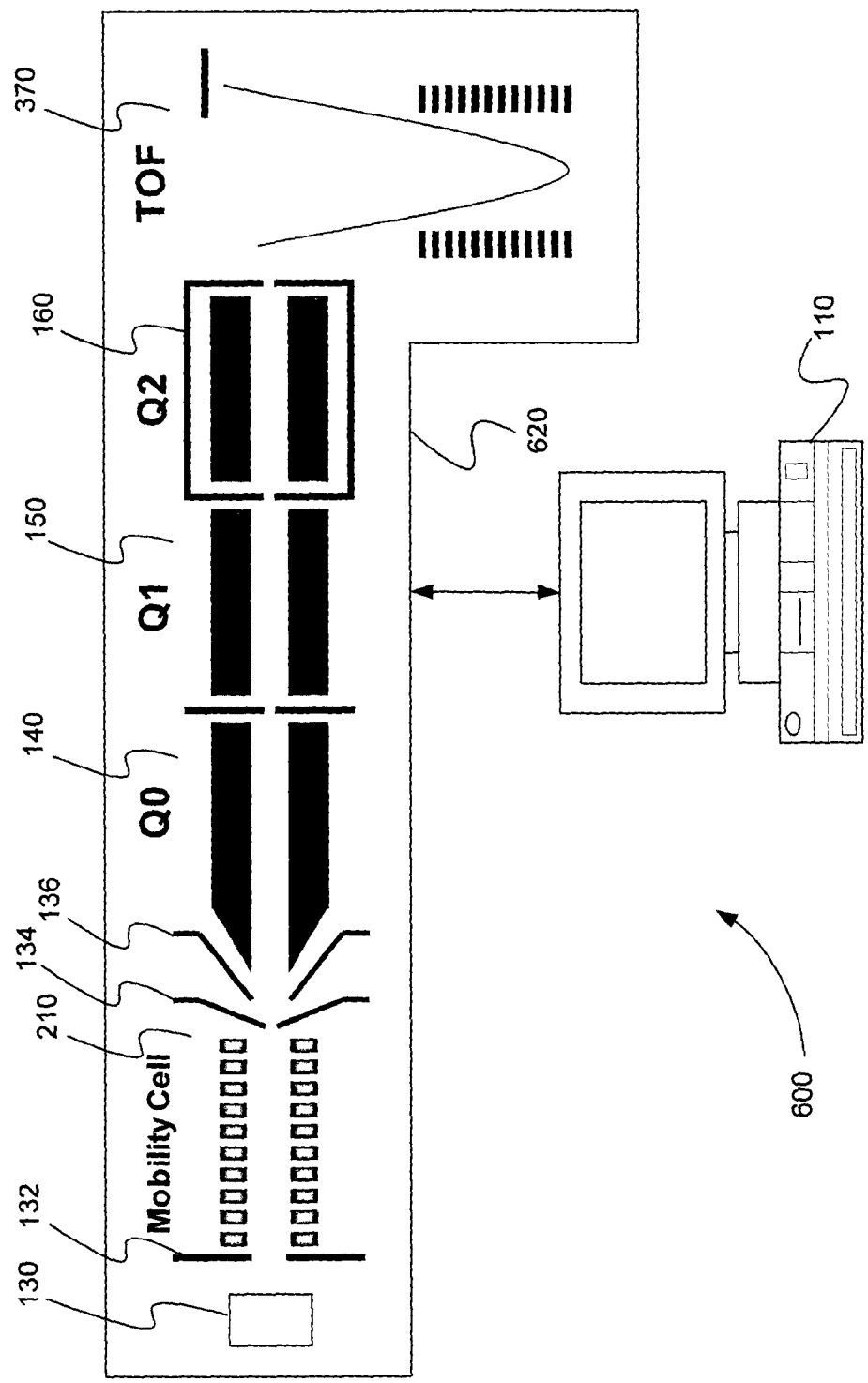
FIG. 6 is a schematic diagram that illustrates a system for targeted ion parking that includes a mobility cell and a quadrupole quadrupole time-of-flight (QqTOF) system, in accordance with various embodiments.

FIG. 6 is a schematic diagram that illustrates a system 600 for targeted ion parking that includes a mobility cell and a quadrupole quadrupole time-of-flight (QqTOF) mass spectrometer 620, in accordance with various embodiments. In system 600, mobility cell 210 is used to select and transmit a subset of the ionized molecules of a sample based on ion mobility. The subset of the ionized molecules is then charge reduced and parked in quadrupole 160, for example. Time-of-flight (TOF) chamber 370 is used for mass analysis or fragmentation, for example.

In various embodiments, system 600 can be used to perform targeted ion parking based on both ion mobility and ion mass. Mobility cell 210 is used to select and transmit a subset of the ionized molecules of a sample based on ion mobility. Quadrupole 150 is used to select and transmit a subset of the mobility selected ionized molecules based on ion mass to quadrupole 160, where the subset of the ionized molecules is charge reduced and parked, for example.

Figure 7:
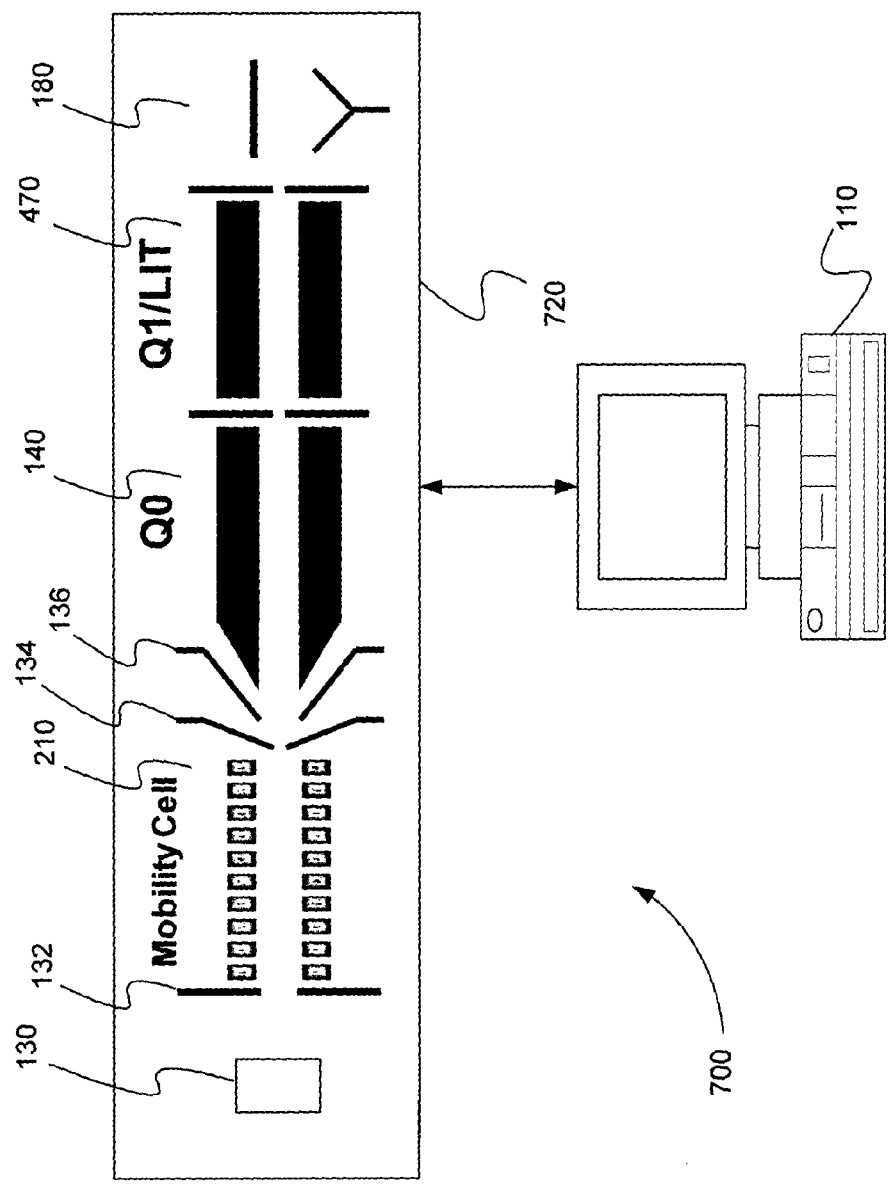
FIG. 7 is a schematic diagram that illustrates a system for targeted ion parking that includes a mobility cell and a quadrupole linear ion trap (QLIT) system, in accordance with various embodiments.

FIG. 7 is a schematic diagram that illustrates a system 700 for targeted ion parking that includes a mobility cell and a quadrupole linear ion trap (QLIT) mass spectrometer 720, in accordance with various embodiments. In system 700, mobility cell 210 is used to select and transmit a subset of the ionized molecules of a sample based on ion mobility. The subset of the ionized molecules is then charge reduced and parked in quadrupole 140, for example. Linear ion trap (LIT) chamber 470 is used for mass analysis or fragmentation, for example.

In various embodiments, system 700 can be used to perform targeted ion parking based on both ion mobility and ion mass. Mobility cell 210 is used to select and transmit a subset of the ionized molecules of a sample based on ion mobility. Chamber 470 is used to select and transmit a subset of the mobility selected ionized molecules based on ion mass to quadrupole 140, where the subset of the ionized molecules is charge reduced and parked, for example.

Figure 8:
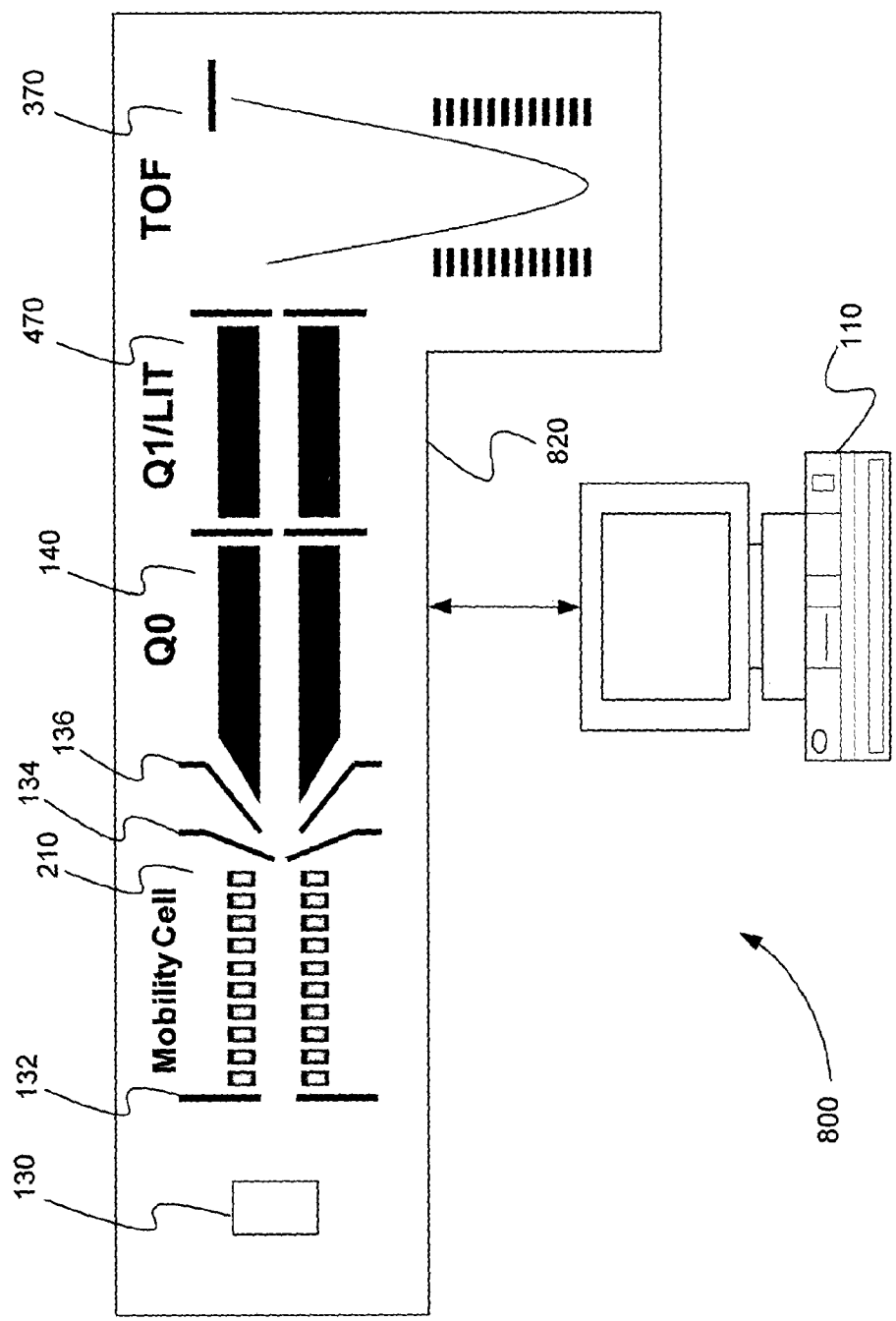
FIG. 8 is a schematic diagram that illustrates a system for targeted ion parking that includes a mobility cell and a quadrupole linear ion trap time-of-flight (QLITTOF) system, in accordance with various embodiments.

FIG. 8 is a schematic diagram that illustrates a system 800 for targeted ion parking that includes a mobility cell and a quadrupole linear ion trap time-of-flight (QLITTOF) mass spectrometer 820, in accordance with various embodiments. In system 800, mobility cell 210 is used to select and transmit a subset of the ionized molecules of a sample based on ion mobility. The subset of the ionized molecules is then charge reduced and parked in quadrupole 140, for example. Time-of-flight (TOF) chamber 370 is used for mass analysis or fragmentation, for example.

In various embodiments, system 800 can be used to perform targeted ion parking based on both ion mobility and ion mass. Mobility cell 210 is used to select and transmit a subset of the ionized molecules of a sample based on ion mobility. Chamber 470 is used to select and transmit a subset of the mobility selected ionized molecules based on ion mass to quadrupole 140, where the subset of the ionized molecules is charge reduced and parked, for example.

Figure 9:
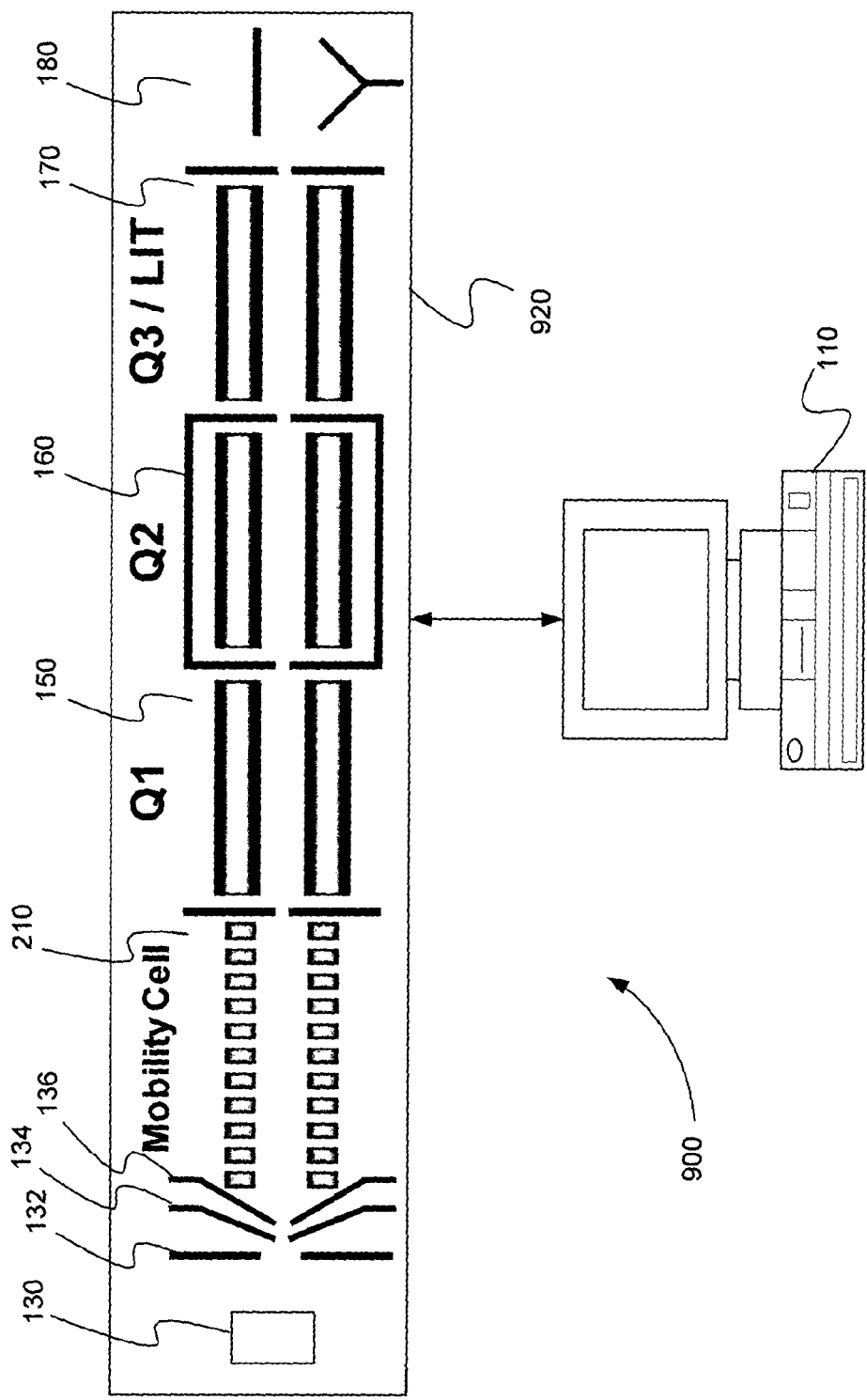
FIG. 9 is a schematic diagram that illustrates a system for targeted ion parking that includes a mobility cell and a hybrid triple quadrupole linear ion trap (QqQLIT) system, where mobility selection is performed at reduced pressure and can be performed before mass selection, in accordance with various embodiments.

FIG. 9 is a schematic diagram that illustrates a system 900 for targeted ion parking that includes a mobility cell and a hybrid quadrupole linear ion trap (QqQLIT) mass spectrometer 920, where mobility selection is performed at reduced pressure and can be performed before mass selection, in accordance with various embodiments. In system 900, mobility cell 210 is used to select and transmit a subset of the ionized molecules of a sample based on ion mobility at reduced pressure. Reduced pressure is, for example, less than one Torr. Mobility cell 210 is located between skimmer 136 and quadrupole 150. The subset of the ionized molecules is then charge reduced and parked in quadrupole 160, for example. Linear ion trap (LIT) chamber 170 is used for mass analysis or fragmentation, for example.

In various embodiments, system 900 can be used to perform targeted ion parking based on both ion mobility and ion mass. Mobility cell 210 is used to select and transmit a subset of the ionized molecules of a sample based on ion mobility. Quadrupole 150 is used to select and transmit a subset of the mobility selected ionized molecules based on ion mass to quadrupole 160, where the subset of the ionized molecules is charge reduced and parked, for example.

Figure 10:
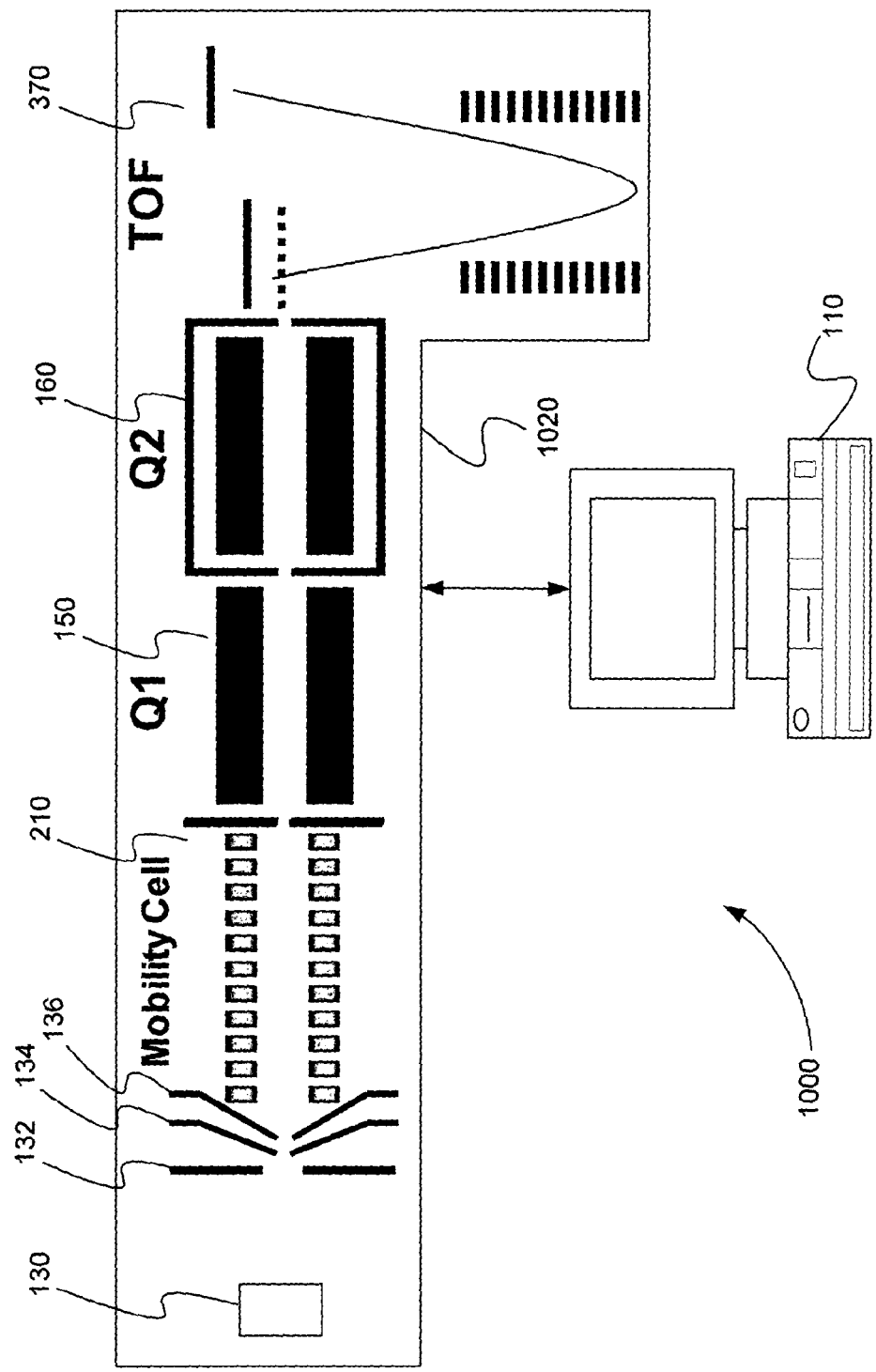
FIG. 10 is a schematic diagram that illustrates a system for targeted ion parking that includes a mobility cell and a hybrid quadrupole time-of-flight (QqTOF) system, where mobility selection is performed at reduced pressure and can be performed before mass selection, in accordance with various embodiments.

FIG. 10 is a schematic diagram that illustrates a system 1000 for targeted ion parking that includes a mobility cell and a hybrid quadrupole time-of-flight (QqTOF) mass spectrometer 1020, where mobility selection is performed at reduced pressure and can be performed before mass selection, in accordance with various embodiments. In system 1000, mobility cell 210 is used to select and transmit a subset of the ionized molecules of a sample based on ion mobility at reduced pressure. The subset of the ionized molecules is then charge reduced and parked in quadrupole 160, for example. Time-of-flight (TOF) chamber 370 is used for mass analysis or fragmentation, for example.

In various embodiments, system 1000 can be used to perform targeted ion parking based on both ion mobility and ion mass. Mobility cell 210 is used to select and transmit a subset of the ionized molecules of a sample based on ion mobility. Quadrupole 150 is used to select and transmit a subset of the mobility selected ionized molecules based on ion mass to quadrupole 160, where the subset of the ionized molecules is charge reduced and parked, for example.

Figure 11:
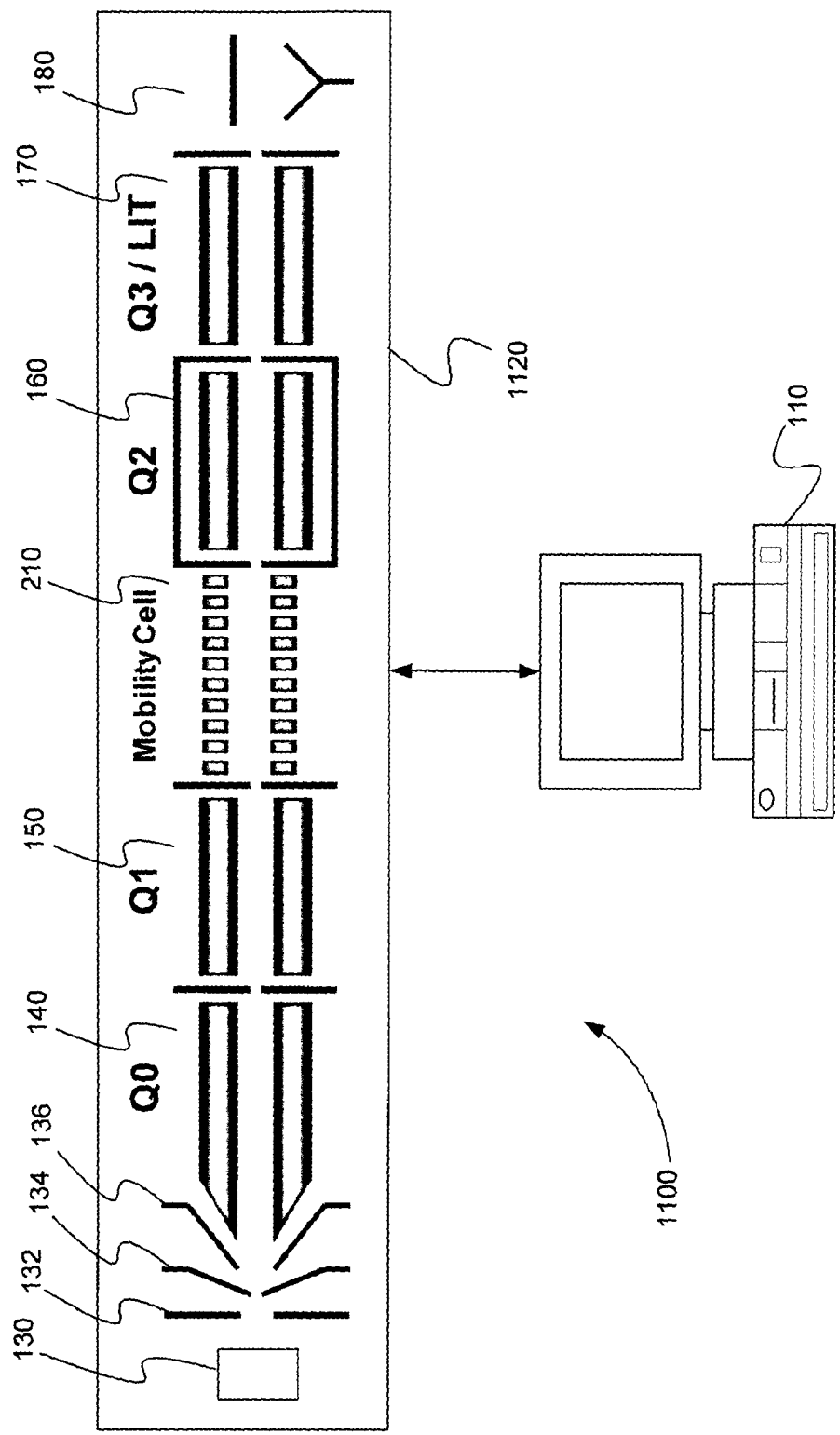
FIG. 11 is a schematic diagram that illustrates a system for targeted ion parking that includes a mobility cell and a hybrid quadrupole linear ion trap (QqQLIT) system, where mobility selection is performed at reduced pressure and can be performed after mass selection, in accordance with various embodiments.

FIG. 11 is a schematic diagram that illustrates a system 1100 for targeted ion parking that includes a mobility cell and a hybrid quadrupole linear ion trap (QqQLIT) mass spectrometer 1120, where mobility selection is performed at reduced pressure and can be performed after mass selection, in accordance with various embodiments. In system 1100, mobility cell 210 is used to select and transmit a subset of the ionized molecules of a sample based on ion mobility at reduced pressure. Mobility cell 210 is located between quadrupole 150 and quadrupole 160. The subset of the ionized molecules is then charge reduced and parked in quadrupole 160, for example. Linear ion trap (LIT) chamber 170 is used for mass analysis or fragmentation, for example.

In various embodiments, system 1100 can be used to perform targeted ion parking based on both ion mobility and ion mass. Quadrupole 150 is used to select and transmit a subset of the ionized molecules of a sample based on ion mass. Mobility cell 210 is used to select and transmit a subset of the mass selected ionized molecules based on ion mobility to quadrupole 160, where the subset of the ionized molecules is charge reduced and parked, for example.

Figure 12:
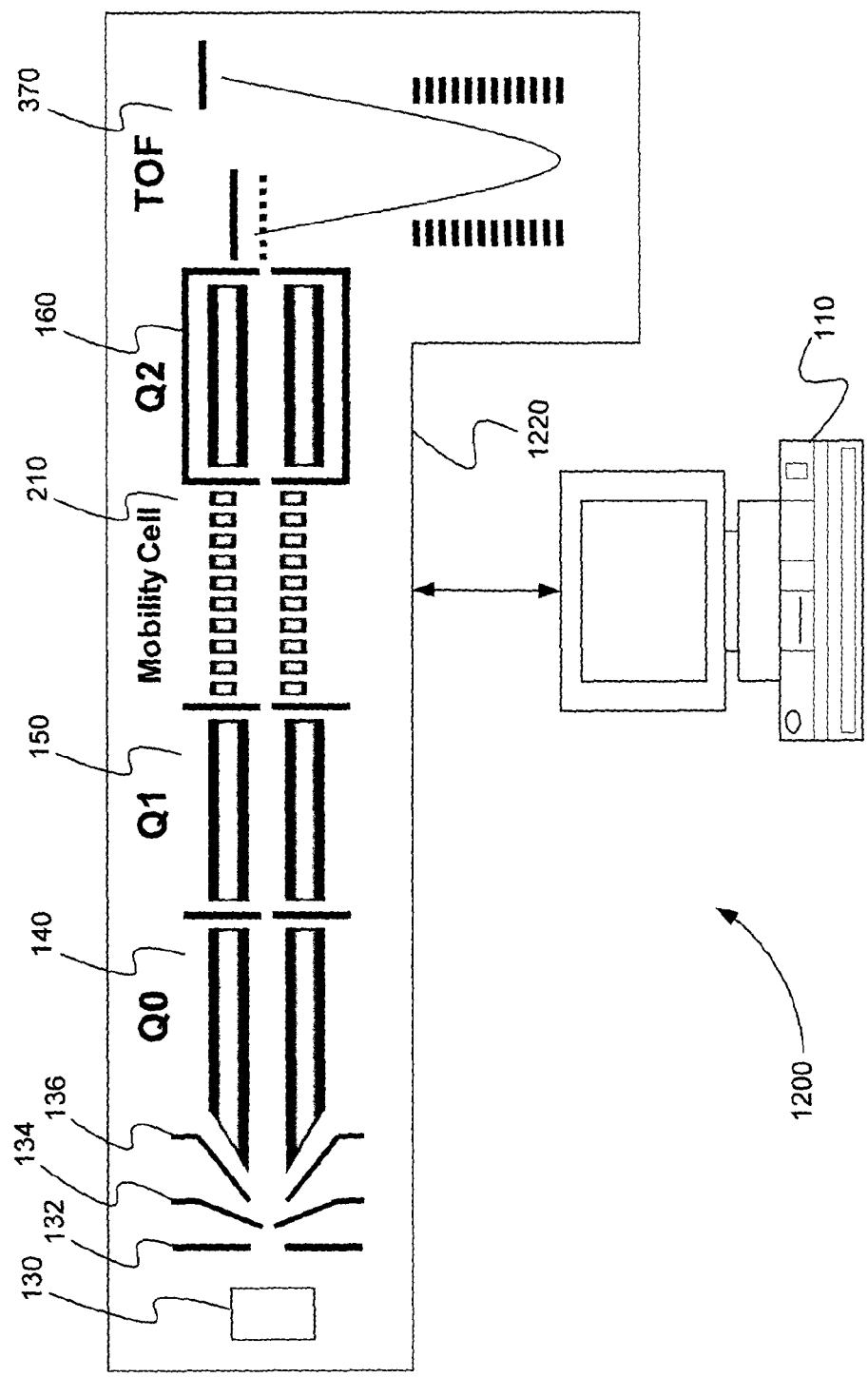
FIG. 12 is a schematic diagram that illustrates a system for targeted ion parking that includes a mobility cell and a hybrid quadrupole time-of-flight (QqTOF) system, where mobility selection is performed at reduced pressure and can be performed after mass selection, in accordance with various embodiments.

FIG. 12 is a schematic diagram that illustrates a system 1200 for targeted ion parking that includes a mobility cell and a hybrid quadrupole time-of-flight (QqTOF) mass spectrometer 1220, where mobility selection is performed at reduced pressure and can be performed after mass selection, in accordance with various embodiments. In system 1200, mobility cell 210 is used to select and transmit a subset of the ionized molecules of a sample based on ion mobility at reduced pressure. Mobility cell 210 is located between quadrupole 150 and quadrupole 160. The subset of the ionized molecules is then charge reduced and parked in quadrupole 160, for example. Time-of-flight (TOF) chamber 370 is used for mass analysis or fragmentation, for example.

In various embodiments, system 1200 can be used to perform targeted ion parking based on both ion mobility and ion mass. Quadrupole 150 is used to select and transmit a subset of the ionized molecules of a sample based on ion mass. Mobility cell 210 is used to select and transmit a subset of the mass selected ionized molecules based on ion mobility to quadrupole 160, where the subset of the ionized molecules is charge reduced and parked, for example.

Figure 13:
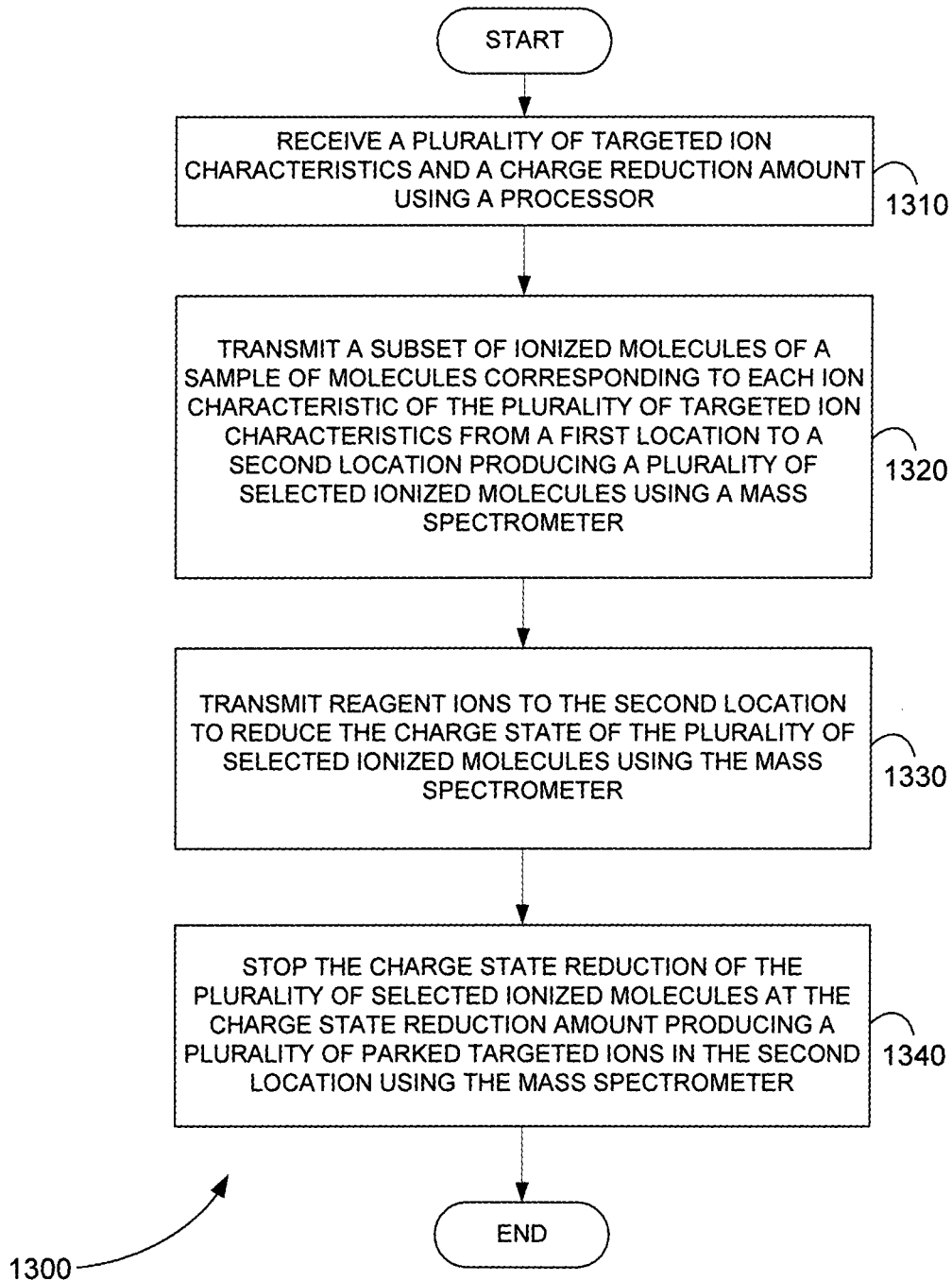
FIG. 13 is a flowchart showing a method for targeted ion parking based ion mobility or ion mass using a mass spectrometer, in accordance with various embodiments.

FIG. 13 is a flowchart showing a method 1300 for targeted ion parking based ion mobility or ion mass using a mass spectrometer, in accordance with various embodiments.

In step 1310 of method 1300, a plurality of targeted ion characteristics and a charge reduction amount are received using a processor. The plurality of targeted ion characteristics can include, but is not limited to, a plurality of targeted ion mobilities or a plurality of targeted mass-to-charge ratios.

In step 1320, a subset of ionized molecules of a sample of molecules corresponding to each ion characteristic of the plurality of targeted ion characteristics is transmitted from a first location to a second location, producing a plurality of selected ionized molecules using a mass spectrometer. If the targeted ion characteristics include a plurality of targeted ion mobilities, the first location can be a mobility cell, for example. If the targeted ion characteristics include a plurality of targeted mass-to-charge ratios, the first location can be a quadrupole, for example. If the targeted ion characteristics include a plurality of targeted mass-to-charge ratios, each subset of ionized molecules can be selected and transmitted to the second location by applying a specific RFDC voltage to the quadrupole.

In step 1330, reagent ions are transmitted to the second location to reduce the charge state of the plurality of selected ionized molecules using the mass spectrometer. The plurality of reagent ions is also transmitted from the first location to the second location, for example. A quadrupole, for example, is used to transmit the plurality of reagent ions from the first location to the second location. The second location can be, for example, a collision cell.

In step 1340, the charge state reduction of the plurality of selected ionized molecules is stopped at the charge state reduction amount, producing a plurality of parked targeted ions in the second location using the mass spectrometer. In various embodiments, the mass spectrometer of method 1300 can include, but is not limited to including, a triple quadrupole, an ion trap, or a time-of-flight spectrometer.

In various embodiments, the plurality of parked targeted ions produced in step 1340 can be used in additional ion processing. Additional ion processing can include, but is not limited to, mass analysis or fragmentation. In various embodiments, the plurality of parked targeted ions produced in step 1340 can be used for mass spectrometry mass spectrometry (MSMS). In various embodiments, the plurality of parked targeted ions produced in step 1340 can be used to identify an analyte.

In various embodiments, method 1300 can be used for quantitation. The sample of molecules described in step 1320 can include a standard group of molecules with a known concentration of an analyte. Quantitation can then be performed according to the additional following steps.

In an additional step not shown, a plurality of mass-to-charge ratios of the plurality of parked targeted ions found in step 1340 are detected and intensities of the plurality of mass-to-charge ratios are measured using the mass spectrometer.

In an additional step (not shown), an additional plurality of standard groups of molecules with known concentrations of the analyte is analyzed, each standard group of the additional plurality of standard groups is used as the sample, and steps 1320-1340 or the above additional step not shown are repeated for each standard group using the mass spectrometer. A calibration function is compiled that relates analyte concentration to intensities of the plurality of reduced mass-to-charge ratios using the processor.

In an additional step (not shown), a collection of ionized molecules with an unknown concentration of the analyte is analyzed and using the collection as the sample, steps 1320-1340 or the above not shown steps are repeated using the mass spectrometer. A concentration of the analyte in the collection is determined from the measured intensities of the plurality of reduced mass-to-charge ratios and the calibration function using the processor.

The use of a mobility cell or quadrupole in method 1300 can improve the selectivity of the ionized molecules that are charge reduced in comparison to the method disclosed in the Afeyan patent, for example. Similarly, performing isolation and charge reduction in separate chambers of the mass spectrometer allows all of the charge states of the ionized molecules to be accumulated before charge reduction, thereby improving the overall throughput of method 1300 in comparison to the method disclosed in the Afeyan patent, for example.

Figure 14:
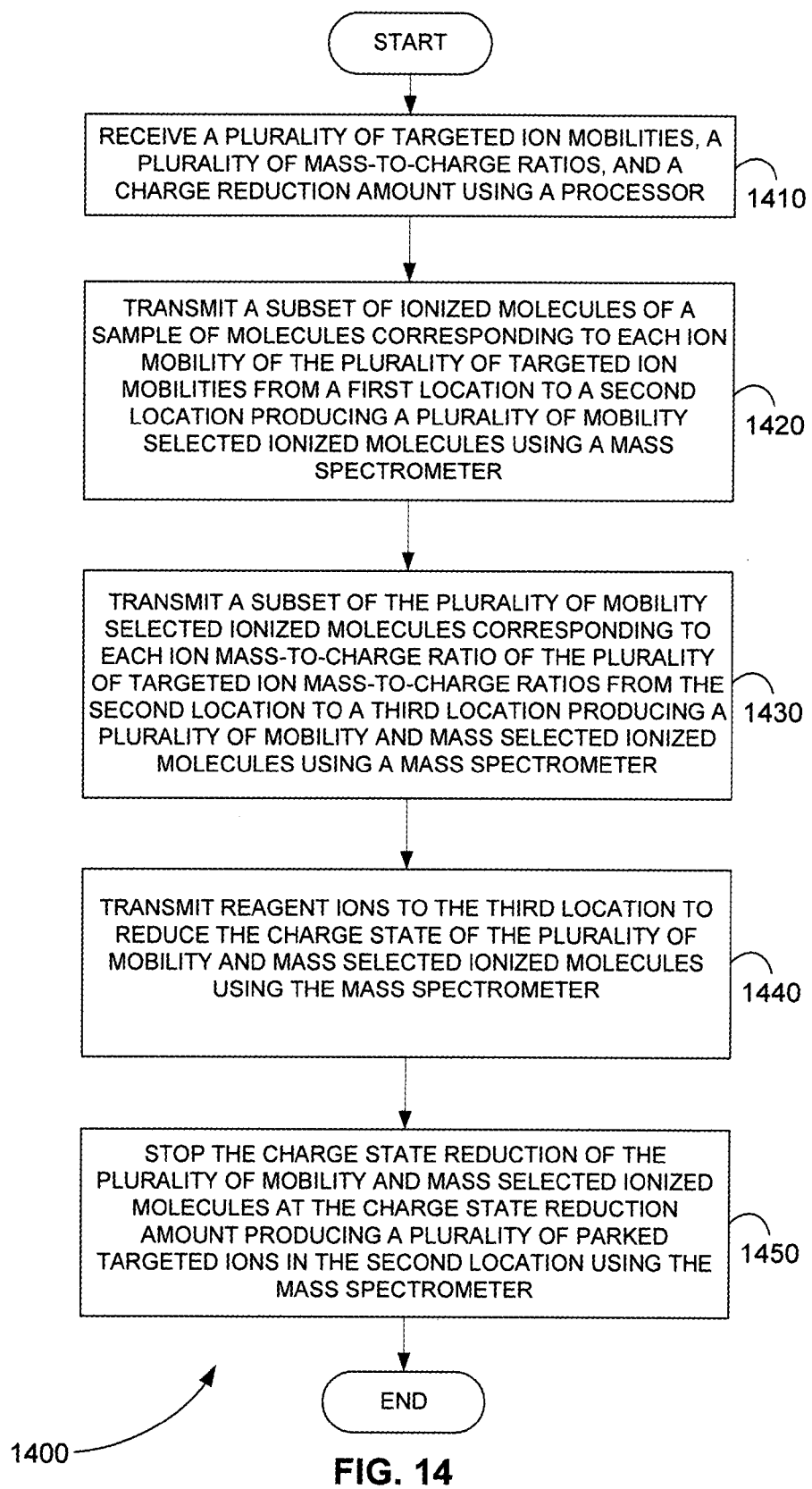
FIG. 14 is a flowchart showing a method for targeted ion parking based on ion mobility and mass selection where mobility selection is performed before mass selection using a mass spectrometer, in accordance with various embodiments.

FIG. 14 is a flowchart showing a method 1400 for targeted ion parking based on ion mobility and mass selection where mobility selection is performed before mass selection using a mass spectrometer, in accordance with various embodiments.

In step 1410 of method 1400, a plurality of targeted ion mobilities, a plurality of targeted ion mass-to-charge ratios, and a charge reduction amount are received using a processor.

In step 1420, a subset of ionized molecules of a sample of molecules corresponding to each ion mobility of the plurality of targeted ion mobilities is transmitted from a first location to a second location, producing a plurality of mobility selected ionized molecules using a mass spectrometer.

In step 1430, a subset of the plurality of mobility selected ionized molecules corresponding to each ion mass-to-charge ratio of the plurality of targeted ion mass-to-charge ratios is transmitted from the second location to a third location, producing a plurality of mobility and mass selected ionized molecules using a mass spectrometer.

In step 1440, reagent ions are transmitted to the third location to reduce the charge state of the plurality of mobility and mass selected ionized molecules using the mass spectrometer.

In step 1450, the charge state reduction of the plurality of mobility and mass selected ionized molecules is stopped at the charge state reduction amount, producing a plurality of parked targeted ions in the third location using the mass spectrometer. In various embodiments, the plurality of parked targeted ions produced in step 1450 can be used in additional ion processing. Additional ion processing can include, but is not limited to, mass analysis or fragmentation.

Figure 15:
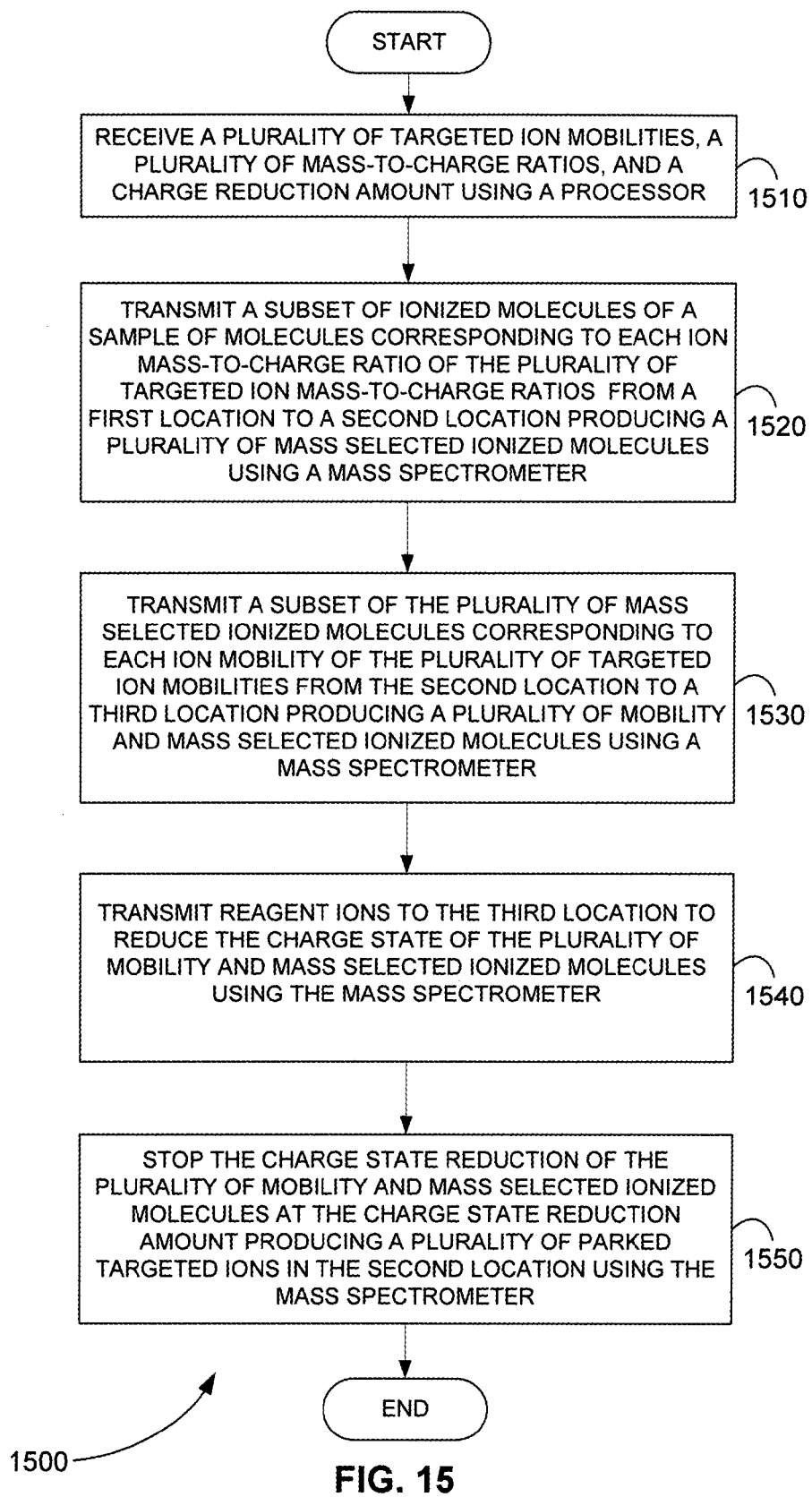
FIG. 15 is a flowchart showing a method for targeted ion parking based on ion mobility and mass selection where mass selection is performed before mobility selection using a mass spectrometer, in accordance with various embodiments.

FIG. 15 is a flowchart showing a method 1500 for targeted ion parking based on ion mobility and mass selection where mass selection is performed before mobility selection using a mass spectrometer, in accordance with various embodiments.

In step 1510 of method 1500, a plurality of targeted ion mobilities, a plurality of targeted ion mass-to-charge ratios, and a charge reduction amount are received using a processor.

In step 1520, a subset of ionized molecules of a sample of molecules corresponding to each mass-to-charge ratio of the plurality of targeted ion mass-to-charge ratios is transmitted from a first location to a second location, producing a plurality of mass selected ionized molecules using a mass spectrometer.

In step 1530, a subset of the plurality of mass selected ionized molecules corresponding to each ion mobility of the plurality of targeted ion mobilities is transmitted from the second location to a third location, producing a plurality of mobility and mass selected ionized molecules using a mass spectrometer.

In step 1540, reagent ions are transmitted to the third location to reduce the charge state of the plurality of mobility and mass selected ionized molecules using the mass spectrometer.

In step 1550, the charge state reduction of the plurality of mobility and mass selected ionized molecules is stopped at the charge state reduction amount, producing a plurality of parked targeted ions in the third location using the mass spectrometer. In various embodiments, the plurality of parked targeted ions produced in step 1550 can be used in additional ion processing. Additional ion processing can include, but is not limited to, mass analysis or fragmentation.

Windowed Ion-Ion Reactions for Noise Reduction

As described above with regard to targeted ion parking, a subset of ions generated from an ion source are selected in a first location of a mass spectrometer and transmitted to second location of the mass spectrometer for ion parking. The selection of ions is based on one or more masses of a known compound, mobilities of a known compound, or both the masses and mobilities of a known compound, for example.

Ion parking involves reducing the charge state of the subset of ions in the second location through ion to ion (ion-ion) charge transfer reaction by a specified amount. The specified amount is the charge state difference, or charge state reduction amount. In other words, the specified amount is a number of charges, or total change in charge state, desired for a compound of interest, for example. A total change in charge state can be obtained by stopping the ion-ion charge transfer reaction for ions that reach that change in charge state. The ion-ion charge transfer reaction is stopped, for example, for ions with a particular mass-to-charge ratio by resonant excitation at that mass-to-charge ratio.

Targeted ion parking is well suited for analyzing known compounds. However, it less practical for use in identifying unknown compounds from chemical noise.

In various embodiments, a windowed mass spectrometry method is combined with ion-ion reactions in order to identify compounds from chemical noise. In particular, subsets of ions are selected using a series of mass-to-charge (m/z) window widths across an m/z range. The window widths are selected in a first location of the spectrometer, for example. The ions resulting from the selection are then transmitted to a second location for ion-ion reaction with a reagent. The ion-ion reaction shifts the m/z of multiply charged ions in the second location to a higher m/z value. The ions resulting from the ion-ion reaction with the reagent are then mass analyzed.

In one embodiment, the chemical noise includes multiply charged ions and the analytes of interest include singly charged ions. In this embodiment, unknown compounds are identified from the resulting spectrum at m/z values less than or equal to the highest m/z value of the m/z window width used in the first location.

In another embodiment, the chemical noise includes singly charged ions and the analytes of interest include multiply charged ions. In this embodiment, unknown compounds are identified from the resulting spectrum at m/z values greater than the highest m/z value of the m/z window width used in the first location. There is little interference at these higher m/z values, because the selected m/z window width prevented compounds at higher m/z from being selected.

More specifically, in various embodiments ion-ion charge transfer reactions (CTR) are used to distinguish analyte ions from other analyte ions or from chemical noise ions. For example, a reagent ion is selected that reduces the charge state of multiply charged ions and thus moves their peaks to a higher m/z-range while leaving the charge state of the remaining ions unaffected. It is well known that ions with a higher charge state are reduced faster in ion-ion transfer reactions than ions with a lower charge state. As a result, multiply charged ions are charged reduced well before singly charged ions in an ion-ion CTR.

A mass range of interest is divided into several mass window widths. Each mass window width is selected in a first location of a mass spectrometer. The first location is, for example, Q1 of a quadrupole device. An ion-ion transfer reaction is performed in a second location of the mass spectrometer. The second location is, for example, Q2 of a quadrupole device. The resultant mixture of product ions in the second location is mass analyzed. The resultant mixture is mass analyzed using a quadrupole, a linear trap or an orthogonal TOF, for example. Depending on reagent ions, reaction in the second location can be performed 'on the fly' (~10 ms time scale) as a flow-through technique, or ions can be temporarily trapped in the second location to allow more time for the reaction to proceed.

For example, using small window widths in the first location, only a small portion (e.g., 25-50 Th) of ions produced by ESI of the compound-containing solution are transmitted to the second location. With this small m/z range of ions trapped, a proton-transfer reaction (PTR)—or more generically, a charge-transfer reaction (CTR)—is initiated resulting in a mass spectrum containing charge-reduced ions with m/z values higher than that of the original Q1 window. If the transferred m/z window is set from "a" to "b", ions with charge up to $z=b/(b-a)$ will be moved to a higher region at m/z>b by means of a single charge loss.

In various embodiments, if the analytes of interest include multiply charged ions and analyte ions are transmitted through the first location, the CTR mass spectrum can contain a distribution of analyte ions with sequential charge states present. Using deconvolution and charge state recognition, the molecular weight of an intact compound can be calculated. Alternatively, if mass resolution of the analyzer permits, charge and therefore molecular weight can be determined by measuring the isotopic spacing of the charge reduced ions.

The low m/z chemical noise ions are deconlvolved from the multiply charged analyte ions by selectively increasing the m/z values of the analyte ions via CTRs. As singly charged ions, chemical noise reacts at a much slower rate than the analyte ions.

As a result, chemical noise is less likely to continue convoluting the analyte mass spectrum after CTR. Charge transfer can include, but is not limited to, proton transfer, electron transfer, or transfer of any anion or cation.

The mass window widths of the mass range of interest can be adjacent or can be separated by gaps in the mass range. Multiply charged analyte compounds can include, but are not limited to, proteins, peptides, oligonucleotides, and polymers.

Various mass spectrometer configurations are shown in FIGS. 1-12 and are described above for use in ion parking. The mass spectrometer configurations shown in FIGS. 1-12 can also be used to windowed ion-ion reactions for noise reduction. More specifically, in various embodiments the mass spectrometer configurations shown in FIGS. 1-12 can be used to identify singly charged ions of a compound from multiply charged chemical noise ions. Alternatively, in various embodiments the mass spectrometer configurations shown in FIGS. 1-12 can be used to identify multiply charged ions of a compound from singly charged chemical noise ions.

For example, system 100 of FIG. 1 can be used to identify a singly charged ion of a compound from multiply charged chemical noise ions. Mass spectrometer 120 selects a plurality of ionized molecules of an ion source that have mass-to-charge ratios within a mass-to-charge ratio window width in a first location. The first location is quadrupole 150. Mass spectrometer 120 transmits the plurality of selected ionized molecules from quadrupole 150 to a second location. The second location is quadrupole 160. Mass spectrometer 120 transmits a plurality of reagent ions to quadrupole 160 to reduce a charge state of one or more of the plurality of selected ionized molecules. Mass spectrometer 120 analyzes the plurality of reduced ionized molecules. Mass spectrometer 120 transmits the plurality of reduced ionized molecules to quadrupole 170 for mass analysis, for example. Mass spectrometer 120 produces a mass spectrum using quadrupole 170 and detector 180.

Processor 110 obtains the mass spectrum produced by mass spectrometer 120. Processor 110 identifies a compound from a mass peak of the mass spectrum that has a mass-to-charge ratio less than or equal to the highest mass-to-charge ratio in the mass-to-charge ratio window width. In other words, processor 110 identifies a compound from a mass peak within the mass-to-charge ratio window width, because the multiply chemical noise has been moved outside of the mass-to-charge ratio window width. In various embodiments, processor 110 additionally searches a database of known compounds for a compound with the peak mass-to-charge ratio.

Similarly, system 100 of FIG. 1 can be used to identify a multiply charged ion of a compound from singly charged chemical noise ions. Mass spectrometer 120 performs all the steps described immediately above. However, processor 110 identifies a compound from a mass peak of the mass spectrum that has a mass-to-charge ratio greater than the highest mass-to-charge ratio in the mass-to-charge ratio window width. In other words, processor 110 identifies a compound from a mass peak above the mass-to-charge ratio window width, because the singly charged chemical noise remains within the mass-to-charge ratio window width.

As above, in various embodiments processor 110 additionally searches a database of known compounds for a compound with the peak mass-to-charge ratio. Processor 110 can also determine if the compound is a known compound in a number of other ways.

In various embodiments, processor 110 locates a second mass peak of the spectrum that has a second peak mass-to-charge ratio within the mass-to-charge ratio window width. Processor 110 identifies the compound from the mass peak and the second mass peak if a difference between the peak mass-to-charge ratio and the second peak mass-to-charge ratio is explained by a reduction in charge state of a mass. Processor 110 further searches a database of known compounds for the mass, for example.

In various embodiments, processor 110 determines the mass of a compound using isotopic peaks. Processor 110 identifies one or more isotopic mass peaks of the mass spectrum near the mass peak. Processor 110 determines the mass of the compound from the mass peak and the one or more isotopic mass peaks.

Figure 16:
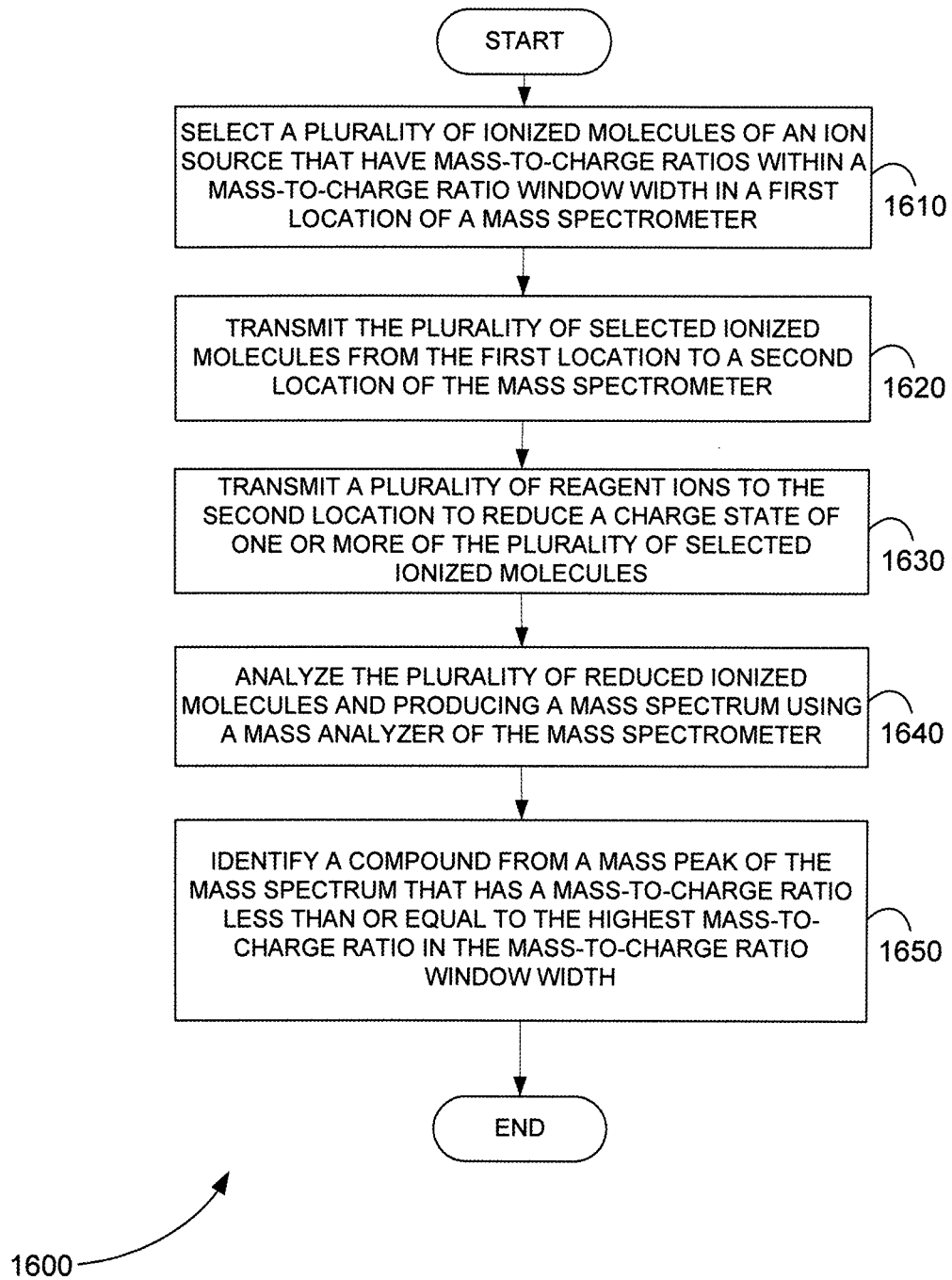
FIG. 16 is a flowchart showing a method for identifying a singly charged ion of a compound from multiply charged chemical noise ions in mass spectrometry, in accordance with various embodiments.

FIG. 16 is a flowchart showing a method 1600 for identifying a singly charged ion of a compound from multiply charged chemical noise ions in mass spectrometry, in accordance with various embodiments.

In step 1610 of method 1600, a plurality of ionized molecules of an ion source that have mass-to-charge ratios within a mass-to-charge ratio window width are selected in a first location of a mass spectrometer.

In step 1620, the plurality of selected ionized molecules are transmitted from the first location to a second location of the mass spectrometer.

In step 1630, a plurality of reagent ions are transmitted to the second location to reduce a charge state of one or more of the plurality of selected ionized molecules.

In step 1640, the plurality of reduced ionized molecules are analyzed and a mass spectrum is produced using a mass analyzer of the mass spectrometer.

In step 1650, identify a compound from a mass peak of the mass spectrum that has a mass-to-charge ratio less than or equal to the highest mass-to-charge ratio in the mass-to-charge ratio window width.

Figure 17:
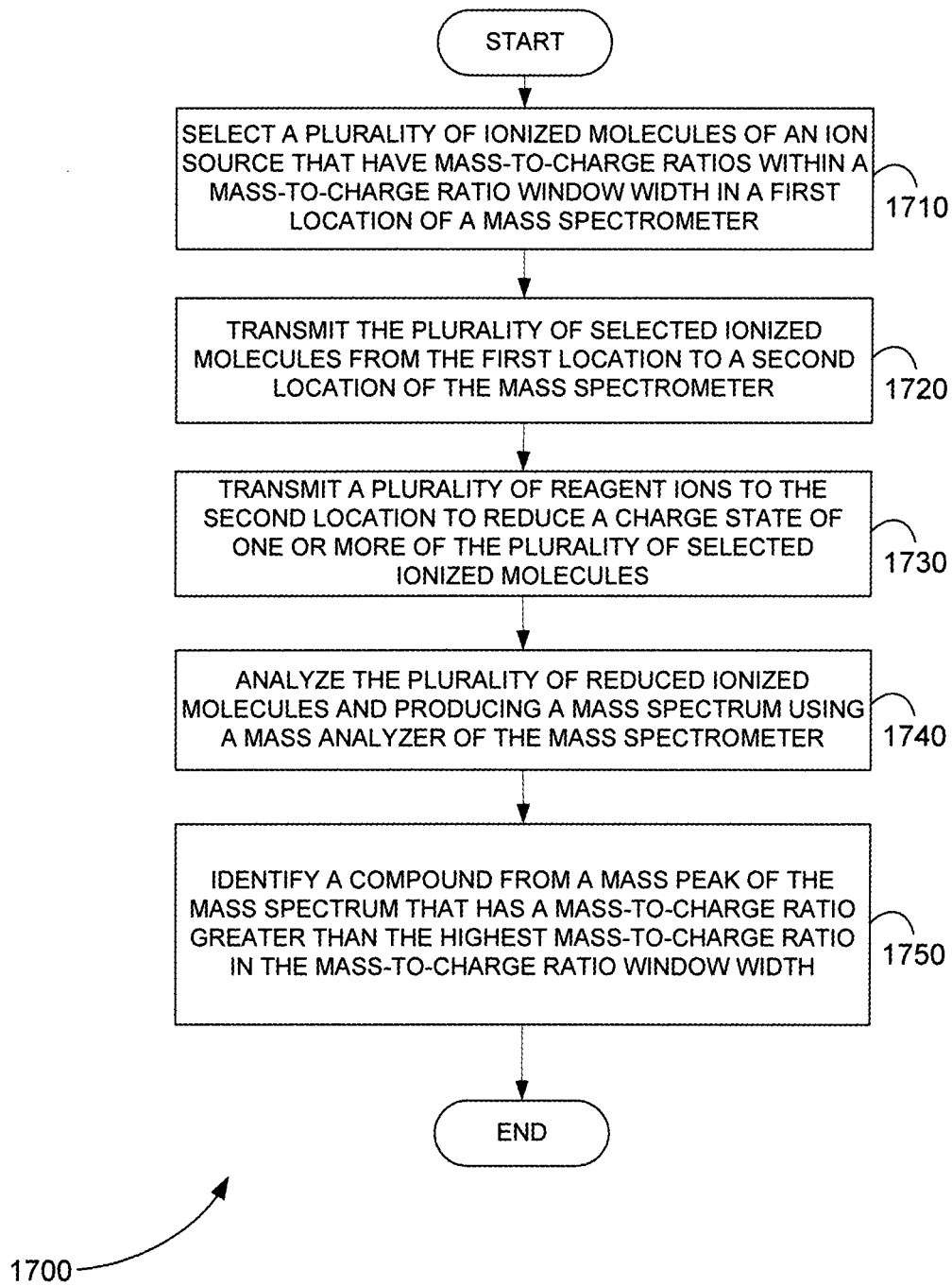
FIG. 17 is a flowchart showing a method for identifying a multiply charged ion of a compound from singly charged chemical noise ions in mass spectrometry, in accordance with various embodiments.

FIG. 17 is a flowchart showing a method 1700 for identifying a multiply charged ion of a compound from singly charged chemical noise ions in mass spectrometry, in accordance with various embodiments.

In step 1710 of method 1700, a plurality of ionized molecules of an ion source that have mass-to-charge ratios within a mass-to-charge ratio window width are selected in a first location of a mass spectrometer.

In step 1720, the plurality of selected ionized molecules are transmitted from the first location to a second location of the mass spectrometer.

In step 1730, a plurality of reagent ions are transmitted to the second location to reduce a charge state of one or more of the plurality of selected ionized molecules.

In step 1740, the plurality of reduced ionized molecules are analyzed and a mass spectrum is produced using a mass analyzer of the mass spectrometer.

In step 1750, identify a compound from a mass peak of the mass spectrum that has a mass-to-charge ratio greater than the highest mass-to-charge ratio in the mass-to-charge ratio window width.

While the applicants' teachings are described in conjunction with various embodiments, it is not intended that the applicants' teachings be limited to such embodiments. On the contrary, the applicants' teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for identifying a multiply charged ion of a compound from singly charged chemical noise ions in mass spectrometry, comprising:
    a mass spectrometer that
        selects a plurality of ionized molecules of an ion source that have mass-to-charge ratios within a mass-to-charge ratio window width in a first location,
        transmits the plurality of selected ionized molecules from the first location to a second location,
        transmits a plurality of reagent ions to the second location to reduce a charge state of one or more of the plurality of selected ionized molecules,
        analyzes the plurality of reduced ionized molecules, and produces a mass spectrum using a mass analyzer; and
    a processor that identifies a compound from a mass peak of the mass spectrum that has a mass-to-charge ratio greater than the highest mass-to-charge ratio in the mass-to-charge ratio window width by
locating a second mass peak of the spectrum that has a second peak mass-to-charge ratio within the mass-to-charge ratio window width, and
identifying the compound from the mass peak and the second mass peak if a difference between the peak mass-to-charge ratio and the second peak mass-to-charge ratio is explained by a reduction in charge state of a mass.

2. The system of claim 1, wherein the processor identifies a compound from a mass peak of the mass spectrum that has a peak mass-to-charge ratio greater than the highest mass-to-charge ratio in the mass-to-charge ratio window width by searching a database of known compounds for a compound with the peak mass-to-charge ratio.

3. The system of claim 1, wherein the processor further searches a database of known compounds for the mass.

4. The system of claim 1, wherein the processor identifies a compound from a mass peak of the mass spectrum that has a peak mass-to-charge ratio greater than the highest mass-to-charge ratio in the mass-to-charge ratio window width by
identifying one or more isotopic mass peaks of the mass spectrum near the mass peak and determining a mass of the compound from the mass peak and the one or more isotopic mass peaks.

5. A method for identifying a multiply charged ion of a compound from singly charged chemical noise ions in mass spectrometry, comprising:
selecting a plurality of ionized molecules of an ion source that have mass-to-charge ratios within a mass-to-charge ratio window width in a first location of a mass spectrometer;
transmitting the plurality of selected ionized molecules from the first location to a second location of the mass spectrometer;
transmitting a plurality of reagent ions to the second location to reduce a charge state of one or more of the plurality of selected ionized molecules;
analyzing the plurality of reduced ionized molecules and producing a mass spectrum using a mass analyzer of the mass spectrometer; and
identifying a compound from a mass peak of the mass spectrum that has a mass-to-charge ratio greater than the highest mass-to-charge ratio in the mass-to-charge ratio window width, comprising
locating a second mass peak of the spectrum that has a second peak mass-to-charge ratio within the mass-to-charge ratio window width, and
identifying the compound from the mass peak and the second mass peak if a difference between the peak mass-to-charge ratio and the second peak mass-to-charge ratio is explained by a reduction in charge state of a mass.

6. The method of claim 5, wherein identifying a compound from a mass peak of the mass spectrum that has a peak mass-to-charge ratio greater than the highest mass-to-charge ratio in the mass-to-charge ratio window width further comprises searching a database of known compounds for a compound with the peak mass-to-charge ratio.

7. The method of claim 5, further comprising searching a database of known compounds for the mass.

8. The method of claim 5, wherein identifying a compound from a mass peak of the mass spectrum that has a peak mass-to-charge ratio greater than the highest mass-to-charge ratio in the mass-to-charge ratio window width further comprises identifying one or more isotopic mass peaks of the mass spectrum near the mass peak and determining a mass of the compound from the mass peak and the one or more isotopic mass peaks.

* * * * *